(12) United States Patent
Kumar et al.

(10) Patent No.: US 9,802,971 B2
(45) Date of Patent: Oct. 31, 2017

(54) ALKANE DEHYDROGENATION PROCESS

(71) Applicants: Akshai Kumar, New Brunswick, NJ (US); Oleg Mironov, San Ramon, CA (US); Robert J. Saxton, San Ramon, CA (US); Alan S. Goldman, Highland, NJ (US)

(72) Inventors: Akshai Kumar, New Brunswick, NJ (US); Oleg Mironov, San Ramon, CA (US); Robert J. Saxton, San Ramon, CA (US); Alan S. Goldman, Highland, NJ (US)

(73) Assignees: Chevron U.S.A. INC., San Ramon, CA (US); Rutgers, The State University of New Jersey, New Brunswick, NJ (US)

( * ) Notice: Subject to any disclaimer, the term of this patent is extended or adjusted under 35 U.S.C. 154(b) by 103 days.

(21) Appl. No.: 14/638,997

(22) Filed: Mar. 4, 2015

(65) Prior Publication Data
US 2015/0251171 A1 Sep. 10, 2015

Related U.S. Application Data

(60) Provisional application No. 61/947,915, filed on Mar. 4, 2014.

(51) Int. Cl.
 *C07C 5/52* (2006.01)
 *C07F 15/00* (2006.01)
 *B01J 31/24* (2006.01)
(52) U.S. Cl.
 CPC ....... *C07F 15/0033* (2013.01); *B01J 31/2409* (2013.01); *C07C 5/52* (2013.01);
 (Continued)

(58) Field of Classification Search
 CPC .............. C07F 15/0033; B01J 31/2409; B01J 2531/0244; B01J 2231/766; B01J 2531/827; C07C 5/52; C07C 2531/24
 See application file for complete search history.

(56) References Cited

U.S. PATENT DOCUMENTS 2,620,347 A 12/1952 Rottig et al.
4,805,561 A 2/1989 Davis et al.
(Continued)

OTHER PUBLICATIONS

Xu et al., "Thermochemical alkane dehydrogenation catalyzed in solution without the use of a hydrogen acceptor" Chem. Commun., 23 (1997): 2273-2274.*
(Continued)

*Primary Examiner* — Brian McCaig
*Assistant Examiner* — Jason Chong
(74) *Attorney, Agent, or Firm* — E. Joseph Gess; Melissa M. Hayworth

(57) ABSTRACT

Disclosed herein are processes for dehydrogenation of an alkane to an alkene using an iridium pincer complex. In the dehydrogenation reactions, hydrogen that is co-formed during the process must be removed for the chemical reaction to proceed and to prevent the excess hydrogen from poisoning the catalyst. In one embodiment the process comprises providing an alkane feedstock comprising at least one alkane and contacting the alkane with an iridium pincer complex in the presence of a hydrogen acceptor selected from the group consisting of ethylene, propene, or mixtures to form an alkene product. The processes disclosed herein can accomplish facile, low-temperature transfer dehydrogenation of alkanes with unprecedented selectivities and TONs at a reasonable rate of conversion.

13 Claims, 5 Drawing Sheets

(52) U.S. Cl.
CPC .. *B01J 2231/766* (2013.01); *B01J 2531/0244* (2013.01); *B01J 2531/827* (2013.01); *C07C 2531/24* (2013.01)

(56) References Cited

U.S. PATENT DOCUMENTS

| | | | |
|---|---|---|---|
| 4,959,080 | A | 9/1990 | Sternling |
| 5,620,676 | A | 4/1997 | Jacobson et al. |
| 5,780,701 | A | 7/1998 | Kaska et al. |
| 5,811,363 | A | 9/1998 | Leviness et al. |
| 5,817,701 | A | 10/1998 | Leviness |
| 5,821,270 | A | 10/1998 | Chang et al. |
| 6,068,760 | A | 5/2000 | Benham et al. |
| 6,201,030 | B1 | 3/2001 | Beer |
| 6,217,830 | B1 | 4/2001 | Roberts et al. |
| 6,838,487 | B1 | 1/2005 | Demirel et al. |
| 6,880,635 | B2 | 4/2005 | Vinegar et al. |
| 6,982,305 | B2 | 1/2006 | Nagy |
| 9,278,894 | B2 | 3/2016 | Goldman et al. |
| 2010/0236984 | A1* | 9/2010 | Brookhart ............... C07C 5/52 208/121 |
| 2013/0123552 | A1* | 5/2013 | Goldman ............... C07C 5/52 585/3 |

OTHER PUBLICATIONS

International Search Report from corresponding International Application No. PCT/US2015/018818 dated Jun. 19, 2015.
Sabuj Kundu et al., "Sunthesis of piperylene and toluene via transfer dehydrogenation of pentane and pentene", ACS Catal., 2013, vol. 3, pp. 1768-1773.
Zheng Huang et al., Efficient heterogeneous dual catalyst systems for alkane metathesis, Adv. Synth. Catal., 2010, vol. 352, pp. 125-135.
Sabuj Kundu et al., "Rational design and synthesis of highly active pincer-iriduim catalyst for alkane dehydrogenation", Organometallics, 2009, vol. 28, pp. 5432-5444.
Liu, F. et al., "Dehydrogenation of n-Alkanes Catalyzed by Iridium "Pincer" Complexes: Regioselective Formation of α-Olefins", J. Am. Chem. Soc., 1999, 121:4086-4087.
Haibach, M.C., et al., "Alkane metathesis by tandem alkane-dehydrogenation-olefin-metathesis catalysis and related chemistry", Accounts of Chemical Research, 2012, 45(6):947-958.
Belli, J. and Craig M. Jensen, "Catalytic Alkane Dehydrogenation by IrClH2 (PPri3)2: Evidence for an Alkane Associative Mechanism", Organometallics, 1996,15(6):1532-1534.
Göttker-Schnetmann, I., et al., "Synthesis and Properties of Iridium Bis(phosphinite) Pincer Complexes (p-XPCP)IrH2, (p-XPCP)Ir(CO), (p-XPCP)Ir(H)(aryl), and {(p-XPCP)Ir}2{μ-N2} and Their Relevance in Alkane Transfer Dehydrogenation", Organometallics 2004, 23(8):1766-1776.
Leitch, D.C., et al., "Upgrading Light Hydrocarbons via Tandem Catalysis: A Dual Homogeneous Ta/Ir System for Alkane/Alkene Coupling", J. Am. Chem. Soc., 2013,135(28):10302-10305.
Ahuja, R., et al., "Catalytic dehydroaromatization of n-alkanes by pincer-ligated iridium complexes", Nature Chemistry, 2010, 3(2):167-171.
Goldman, A.S. et al., "Catalytic Alkane Metathesis by Tandem Alkane Dehydrogenation-Olefin Metathesis", Science, 2006,312 (5771):257-261.
Göttker-Schnetmann, I. and Maurice Brookhart, "Mechanistic studies of the transfer dehydrogenation of cyclooctane catalyzed by iridium bis(phosphinite) p-XPCP pincer complexes", J. Am. Chem. Soc., 2004,126(30):9330-9338.
Krogh-Jespersen, K., et al., "On the Mechanism of (PCP)Ir-Catalyzed Acceptorless Dehydrogenation of Alkanes: A Combined Computational and Experimental Study", J. Am. Chem. Soc., 2002,124(38):11404-11416.
Göttker-Schnetmann, I., et al., "Iridium Bis(phosphinite)p-XPCP Pincer Complexes: Highly Active Catalysts for the Transfer Dehydrogenation of Alkanes", J. Am. Chem. Soc., 2004,126(6):1804-1811.
Dobereiner, G. E., et al., "Catalytic Synthesis ofn-Alkyl Arenes through Alkyl Group Cross-Metathesis", J. Am. Chem. Soc., 2013,135(34):12572-12575.
Zhu K., et al., "Highly effective pincer-ligated iridium catalysts for alkane dehydrogenation. DFT calculations of relevant thermodynamic, kinetic, and spectroscopic properties", J. Am. Chem. Soc., 2004,126(40):13044-13053.
Choi, J., et al., "Dehydrogenation and related reactions catalyzed by iridium pincer complexes", Chemical Rev., 2011, 111(3):1761-1779.
Renkema, K.B., et al., "Mechanism of alkane transfer-dehydrogenation catalyzed by a pincer-ligated iridium complex", J. Am. Chem. Soc., 2003,125(26):7770-7771.
Shi, Y., et al., "Highly Active Catalysts for the Transfer Dehydrogenation of Alkanes: Synthesis and Application of Novel 7-6-7 Ring-Based Pincer Iridium Complexes". Chem. Eur. J., 2013, 19(32):10672-10689.
Gupta, M., et al., "Catalytic Dehydrogenation of Cycloalkanes to Arenes by a Dihydrido Iridium P—C—P Pincer Complex", J. Am. Chem. Soc., 1997,119(4):840-841.
Fan, Hua-Jun and Michael B. Hall, "Density functional studies of catalytic alkane dehydrogenation by an iridium pincer complex with and without a hydrogen acceptor", Journal of Molecular Catalysis A: Chemical, 2002, 189(1):111-118.
Burk, M. J. and Robert H. Crabtree, "Selective Catalytic Dehydrogenation of Alkanes to Alkenes" J. Am. Chem. Soc., 1987,109 8025.
Huang, Z., et al., "Highly Active and Recyclable Heterogeneous Iridium Pincer Catalysts for Transfer Dehydrogenation of Alkanes", Adv. Synth. Catal., 2009, 351(1-2):188-206.
Crabtree, R.H., et al., "Alkane dehydrogenation by iridium complexes", J. Am. Chem. Soc., 1982,104(1):107-113.
Liu, Fuchen and Alan S. Goldman, "Efficient thermochemical alkane dehydrogenation and isomerization catalyzed by an iridium pincer complex," Chem. Comm. 1999, 655-656.
Jensen, C. M., "Iridium PCP pincer complexes: highly active and robust catalysts for novel homogenous aliphatic dehydrogenations" Chem. Comm. 1999, 2443-2449.
Zhang X. et al., "Novel synthesis of enamines by iridium-catalyzed dehydrogenation of tertiary amines" Chem. Commun. 2003, 2060-2061.
Burk M. J. et al., Thermal and Photochemical Catalytic Dehydrogenation of Alkanes with [IrH2(CF3CO2)(PR3)2] (R=C6H4F-P and Cycolhexyl) J. Chem. Soc., Chem. Commun. 1985, 1829-1830.
Albrecht, M., and Gerard van Koten, "Platinum Group Organometallics Based on "Pincer" complexes: Sensors, Switches, and Catalysts", Angew. Chem. Int. Ed. 40 2001, Wiley-VCH Verlag GmbH, Weinheim, p. 3751.
Singleton, John T., "The uses of pincer complexes in organic synthesis" Tetrahedron 59 2003, 1837-1857.
Gupta, M., et al., "A highly active alkane dehydrogenation catalyst: stabilization of dihydrido rhodium and iridium complexes by a P—C—P pincer ligand" Chem. Commun. 1996, 36, 2083-2084.
Xu, W. et al. "Thermochemical alkane dehydrogenation catalyzed in solution without the use of a hydrogen acceptor" Chem. Commun. 1997, 2273-2274.
Gupta, M., et al., "Catalytic dehydrogenation of ethylbenzene and tetrhydrofunan by a dihydrido iridium P—C—P pincer complex", Chem. Commun. 1997, 461-462.
Ahuja, R., et al., "Catalytic ring expansion, contraction, and metathesis-polymerization of cycloalkanes", Chem. Commun. 2008, 253-255.

* cited by examiner

ALKANE DEHYDROGENATION PROCESS

This application claims priority to U.S. provisional No. 61/947,915 filed Mar. 4, 2014, the contents of which are herein incorporated by reference in their entirety.

FIELD OF ART

Provided is a process for generating olefins (i.e., alkenes) from alkanes. More specifically, the process uses iridium pincer complex catalysts for generating olefins from alkanes.

BACKGROUND

Olefins are an important and versatile feedstock for fuels and chemicals, but they are not as widely available naturally as alkanes. The chemical industry uses olefins as intermediates in a variety of processes. The largest chemical use is linear α-olefins used in the formation of polyolefins such as ethylene-1-octene copolymers. Also and most importantly, low carbon number olefins have the potential to be converted into higher carbon number molecules that would be suitable for fuels, particularly, diesel. Other products formed from olefins include surfactants, lubricants, and plasticizers. Thus, the direct production of alkenes from alkanes via dehydrogenation has drawn great attention. Many heterogeneous catalysts are known to effect dehydrogenation at high temperatures (ca. 500-900° C.), but applications are limited to simple molecules such as ethane or ethylbenzene due to the low selectivity of these catalyst systems. In the case of higher alkanes, lack of selectivity (including catalyst-deactivating coking) severely impacts the utility of dehydrogenation.

Many iridium complexes as catalysts are known. During the 1980s, it was discovered that certain iridium complexes are capable of catalytically dehydrogenating alkanes to alkenes under thermal and photolytic conditions (see, e.g., *J. Am. Chem. Soc.* 104 (1982) 107; 109 (1987) 8025; *J. Chem. Soc., Chem. Commun.* (1985) 1829). For a more recent example, see *Organometallics* 15 (1996) 1532.

Pincer ligand complexes of rhodium and iridium as catalysts for the dehydrogenation of alkanes are receiving widespread attention. See, for example, F. Liu, E. Pak, B. Singh, C. M. Jensen and A. S. Goldman, "Dehydrogenation of n-Alkanes Catalyzed by Iridium "Pincer" Complexes: Regioselective Formation of α-olefins," *J. Am. Chem. Soc.* 1999, 121, 4086-4087; F. Liu and A. S. Goldman, "Efficient thermochemical alkane dehydrogenation and isomerization catalyzed by an iridium pincer complex," *Chem. Comm.* 1999, 655-656; and C. M. Jensen, "Iridium PCP pincer complexes: highly active and robust catalysts for novel homogenous aliphatic dehydrogenations," *Chem. Comm.* 1999, 2443-2449. The use of compounds such as (PCP)MH$_2$ (PCP=C$_6$H$_3$(CH$_2$PBut$_2$)$_2$-2,6) (M=Rh, Ir) dehydrogenate various cycloalkanes to cycloalkenes with turnovers of 70-80 turnovers/hour.

Various pincer catalysts supported on solid supports via polar anchoring groups are also known. See Huang, Z.; Brookhart, M.; Goldman, A. S.; Kundu, S.; Ray, A.; Scott, S. L.; Vicente, B. C. *Adv. Synth. Catal.* 2009, 351, 188 and Huang, Z.; Rolfe, E.; Carson, E. C.; Brookhart, M.; Goldman, A. S.; El-Khalafy, S. H.; MacArthur, A. H. R. *Adv. Synth. Catal.* 2010, 352, 125.

In addition, "pincer" complexes of platinum-group metals have been known since the late 1970s (see, e.g., *J. Chem. Soc., Dalton Trans.* (1976) 1020). Pincer complexes have a metal center and a pincer skeleton. The pincer skeleton is a tridentate ligand that generally coordinates with the meridional geometry. The use of pincer complexes in organic synthesis, including their use as alkane dehydrogenation catalysts, was developed during the 1990s and is the subject of two review articles (see *Angew. Chem. Int. Ed.* 40 (2001) 3751 and *Tetrahedron* 59 (2003)). See also U.S. Pat. No. 5,780,701. Jensen et al. (*Chem. Commun.* 1997 461) used iridium pincer complexes to dehydrogenate ethylbenzene to styrene. Recently, additional pincer complexes have been developed that dehydrogenate hydrocarbons. For some recent examples, see *J. Mol. Catal. A* 189 (2002) 95, 111 and *Chem. Commun.* (1999) 2443.

Initial attempts to design effective homogeneous catalytic systems for alkane dehydrogenation were hampered by catalyst decomposition. In subsequent attempts, Kaska and Jensen reported the first ever robust system for catalytic transfer dehydrogenation of alkanes that was based on a pincer-ligated iridium complex ($^{tBu4}$PCP)Ir(H$_2$). (See, Gupta, M., Hagen, C., Flesher, R. *Chem. Commun.* 1996, 36, 2083-2084 and Gupta, M.; Hagen, C.; Kaska, W. C.; Cramer, R. E.; Jensen, C. M.; Barbara, S. *J. Am. Chem. Soc.* 1997, 267, 840-841.) Later it was observed that both ($^{tBu4}$PCP)Ir (H$_2$) and its isopropyl analog ($^{iPr4}$PCP)Ir(H$_4$) were found to selectively activate C—H bond of alkanes. (See, Liu, F., Pak, E. B., Singh, B., Jensen, C. M., Goldman, A. S. *J. Am. Chem. Soc.* 1999, 121, 4086-4087.) These catalysts were also effective for the acceptorless dehydrogenation of alkanes. (See, Xu, W., Rosini, G. P., Krogh-Jespersen, K., Goldman, A. S., Gupta, M.; Jensen, C. M.; Kaska, W. C. *Chem. Commun.* 1997, 2273-2274; and Liu, F.; Goldman, A. S. Chem. Commun. 1999, 655-656; and Krogh-Jespersen, K.; Czerw, M.; Summa, N.; Renkema, K. B.; Achord, P. D.; Goldman, A. S. *J. Am. Chem. Soc.* 2002, 124, 11404-16.) These studies paved the way for design of several pincer based catalytic systems for alkane dehydrogenation reactions and their mechanistic studies. (See, Renkema, K. B.; Kissin, Y. V; Goldman, A. S. *J. Am. Chem. Soc.* 2003, 125, 7770-1; and Choi, J.; MacArthur, A. H. R.; Brookhart, M.; Goldman, A. S. *Chem. Rev.* 2011, 111, 1761-79; and Haibach, M. C.; Kundu, S.; Brookhart, M.; Goldman, A. S. *Acc. chem. res.* 2012, 45, 947-58.) Over the years many research groups have reported variants of ($^{tBu4}$PCP)Ir(H$_2$) and ($^{iPr4}$PCP)Ir(H$_4$) where either the substituent at the para position of the aryl group has been altered (see Zhu, K.; Achord, P. D.; Zhang, X.; Krogh-Jespersen, K.; Goldman, A. S. *J. Am. Chem. Soc.* 2004, 126, 13044-53; and Huang, Z.; Brookhart, M.; Goldman, A. S.; Kundu, S.; Ray, A.; Scott, S. L.; Vicente, B. C. *Adv. Synth. Catal.* 2009, 351, 188-206) or the CH$_2$ linkers have been modified. (See, Gottker-Schnetmann, I.; Brookhart, M. *J. Am. Chem. Soc.* 2004, 126, 9330-8; and Gottker-Schnetmann, I.; White, P.; Brookhart, M. *J. Am. Chem. Soc.* 2004, 126, 1804-11; and White, P. S.; Brookhart, M.; Hill, C.; Carolina, N. *Organometallics* 2004, 23, 1766-1776; and Ahuja, R.; Punji, B.; Findlater, M.; Supplee, C.; Schinski, W.; Brookhart, M.; Goldman, A. S. *Nat. chem.* 2011, 3, 167-71; and Dobereiner, G. E.; Yuan, J.; Schrock, R. R.; Goldman, A. S.; Hackenberg, J. D. *J. Am. Chem. Soc.* 2013, 135, 12572-5; and Shi, Y.; Suguri, T.; Dohi, C.; Yamada, H.; Kojima, S.; Yamamoto, Y. *Chem. Eur. J.* 2013, 19, 10672-89.) Such phosphine, phosphinite and mixed phosphine-phosphinite based systems have found wide spread utility as catalysts for alkane metathesis (see, Haiback, M. C. Kundu, S.; Brookhart, M.; Goldman, A. S. *Acc. chem. res.* 2012, 45, 947-58; and Goldman, A. S.; Roy, A. H.; Huang, Z.; Ahuja, R.; Schinski, W.; Brookhart, M. *Science* 2006, 312, 257-61; and Ahuja, R.; Kundu, S.;

Goldman, A. S.; Brookhart, M.; Vicente, B. C.; Scott, S. L. *Chem. Commun.* 2008, 253-5), alkyl group metathesis (see, Dobereiner, G. E.; Yuan, J.; Schrock, R. R.; Goldman, A. S.; Hackenberg, J. D. *J. Am. Chem. Soc.* 2013, 135, 12572-5), dehydroaromatization reactions (see, Ahuja, R., Punji, B.; Findlater, M.; Supplee, C.; Schinski, W.; Brookhart, M.; Goldman, A. S. *Nat. chem.* 2011, 3, 167-71), alkane-alkene coupling reactions (see, Leitch, D. C.; Lam, Y. C.; Labinger, J. A; Bercaw, J. E. *J. Am. Chem. Soc.* 2013, 135, 10302-5) and dehydrogenation of several other substrates. (See, Gupta, M.; Kaska, W. C.; Jensen, C. M. *Chem. Commun.* 1997, 461-462; and Jensen, C. M. *Chem. Commun.* 1999, 2443-2449; and Zhang, X.; Fried, A.; Knapp, S.; Goldman, A. S. *Chem. Commun.* 2003, 2060-1.) Recently, there has also been an attempt to understand the steric effects on catalytic efficiency by systematically replacing the phosphino-tert-butyl groups with phosphino methyl groups. (See, Kundu, S.; Choliy, Y.; Zhuo, G.; Ahuja, R.; Emge, T. J.; Warmuth, R.; Brookhart, M.; Krogh-Jespersen, K.; Goldman, A. S. *Organometallics* 2009, 28, 5432-5444.)

One of the widely used hydrogen acceptors for alkane transfer dehydrogenation is tert-butyl ethylene (TBE) as it is resistant to isomerization reactions. However on an industrial scale, the use of TBE is less economical. One would prefer to use hydrogen acceptors that are inexpensive and recyclable.

Despite the extensive research into new catalysts and methods for producing valuable olefin compounds, the search for effective methods to prepare olefins from alkanes continues. Such methods would make the preparation of valuable olefin compounds more economical and efficient.

SUMMARY

Disclosed herein is a process for dehydrogenation of an alkane to an alkene. The process comprises providing an alkane feedstock comprising at least one alkane and contacting the alkane with an iridium pincer complex while removing hydrogen to form an alkene product. The hydrogen can be removed by a using hydrogen acceptor, flowing an inert gas through the reaction, refluxing the reaction in an open container, or conducting the reaction under partial vacuum.

In one embodiment the process comprises providing an alkane feedstock comprising at least one alkane and contacting the alkane with an iridium pincer complex in the presence of a hydrogen acceptor selected from the group consisting of ethylene, propene, or mixtures thereof to form an alkene product.

In another embodiment, the process comprises providing an alkane feedstock comprising at least one alkane, contacting the alkane with an iridium pincer complex to form an alkene product, and immediately converting the alkene product to a secondary product.

The processes disclosed herein can accomplish facile, low-temperature (less than 300° C.) transfer dehydrogenation of alkanes (e.g., highly abundant alkanes like pentane) with unprecedented selectivities and TONs at a reasonable rate of conversion. In certain embodiments the processes use readily recyclable and inexpensive hydrogen acceptors. The processes disclosed herein utilize an iridium pincer complex as a catalyst.

Further disclosed herein are specific iridium pincer complexes. These complexes have particularly efficient for dehydrogenation under the conditions disclosed herein. These iridium pincer complexes include Complex 7: $(^{iPr4}PCP)Ir(C_2H_4)$ and Complex 11: $(p\text{-}OK\text{-}^{iPr4}PCP)Ir(C_3H_6)$.

DETAILED DESCRIPTION

Figure 1:
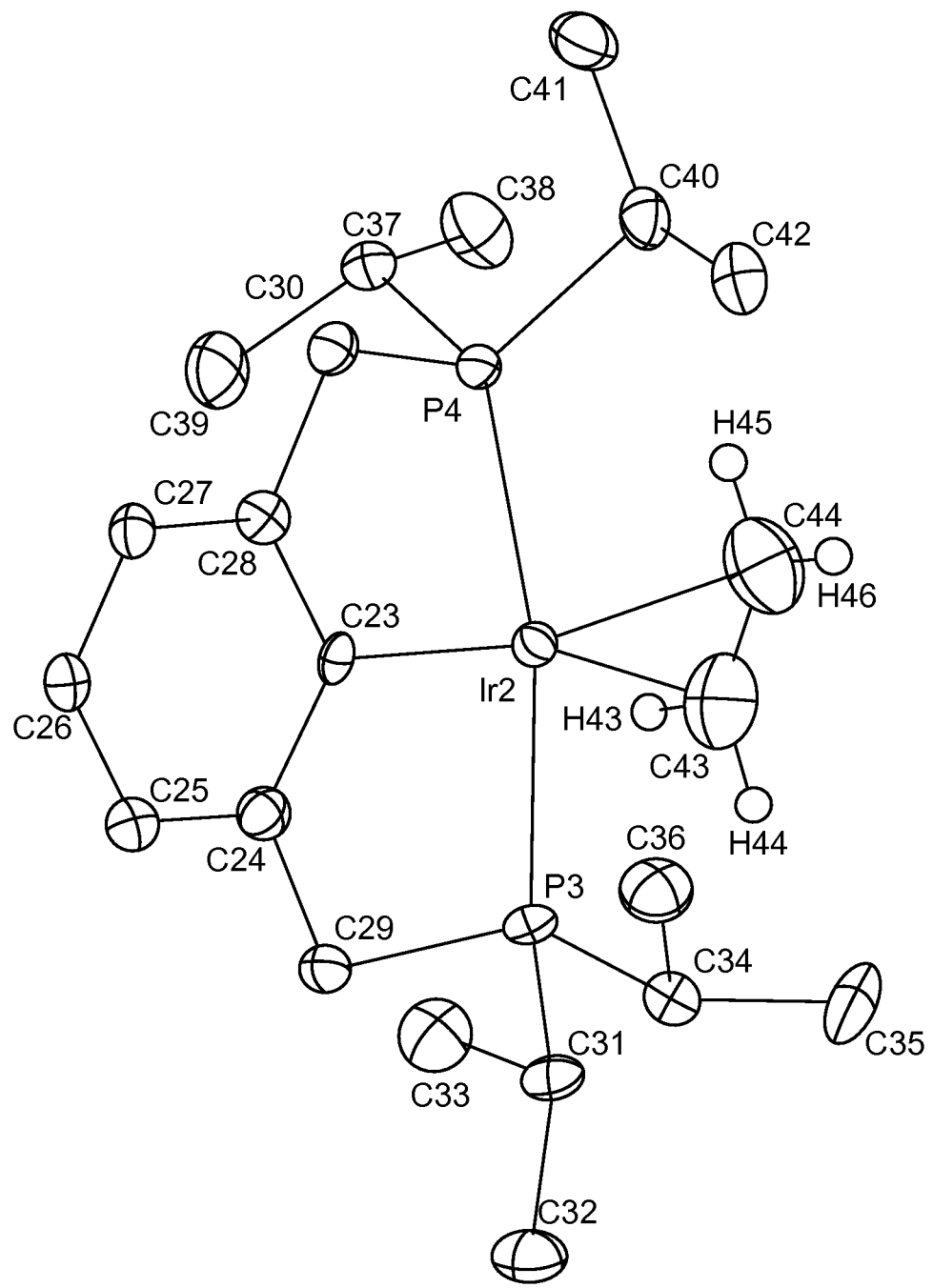
FIG. 1 shows an Oak Ridge Thermal Ellipsoid Plot (ORTEP) diagram of Complex 7: $(^{iPr4}PCP)Ir(C_2H_4)$. Hydrogen atoms are retained only on the ethylene ligand in the drawing.

Provided are processes for dehydrogenation of an alkane to an alkene using an iridium pincer complex. One advantage of the present processes is high selectivity and yield to the same carbon number product as the feed since substantially no cracked products are formed at the low reaction temperatures. Another advantage is the ability to produce odd-carbon number alkene products. With prior art processes, such as ethylene oligomerization, only even-numbered products are obtained. A further advantage is relatively high selectivity to alpha olefin or 1-alkene products.

In the dehydrogenation reactions, hydrogen that is co-formed during the process must be removed for the chemical reaction to proceed and to prevent the excess hydrogen from poisoning the catalyst. The hydrogen can be removed by a using hydrogen acceptor, flowing an inert gas through the reaction, refluxing the reaction in an open container, or conducting the reaction under partial vacuum.

The dehydrogenation processes of the present invention are conducted at lower reaction temperatures. At these lower temperatures, there is substantially no cracking of the alkane feedstock. As such, the processes disclosed herein provide very high selectivity to an alkene product with the same carbon number as the feed at reasonable conversions. The processes exhibit selectivities of greater than 80%. In certain embodiments, the selectivities are 85% and greater. In other embodiments, the selectivities are 90% and greater. In many embodiments, the selectivities are 95% and greater with a reasonable conversion of above 50%. The processes disclosed herein also provide a relatively high selectivity to alpha-olefin or 1-alkene products.

The present processes also exhibit unprecedented TONs. The present processes can show a rate of 100 TON or greater at 10 minutes (based on iridium catalyst) and a turnover frequency (TOF) of 10 min$^{-1}$ or greater. In certain embodiments, the present processes can show a rate of 150 TON or greater at 10 minutes (based on iridium catalyst) and a turnover frequency (TOF) of 15 min$^{-1}$ or greater. In other embodiments, the present processes can show a rate of 200 TON or greater, or 250 TON or greater, at 10 minutes (based on iridium catalyst) and a turnover frequency (TOF) of 20 min$^{-1}$ or greater, or 25 min$^{-1}$ or greater. In certain embodiments, the present processes can show a rate of 500 TON or greater at 10 minutes (based on iridium catalyst) and a turnover frequency (TOF) of 50 min$^{-1}$ or greater.

Embodiments in which a hydrogen acceptor is not utilized are described herein as "non-oxidative" or "acceptor-less". As such these dehydrogenation reactions are conducted in the absence of a hydrogen acceptor with the hydrogen that is co-formed during the process being removed in an alternative way.

In the acceptor-less embodiments, the hydrogen can be removed by sparging (i.e., flowing) an inert gas through the reaction, refluxing the reaction in an open container, and conducting the reaction under partial vacuum.

In an embodiment where the hydrogen is removed by sparging (i.e., flowing), an inert gas is flowed through the reaction medium. An inert gas is one that is unreactive with the iridium pincer complex under reaction conditions. Suitable inert gases include, for example, argon, helium, krypton, and the like.

In some embodiments, nitrogen may work as an inert sparging gas, if it did not inhibit activity of the iridium pincer complex catalyst.

In other embodiments, methane can be used as an inert sparging gas. Methane is typically used as a source for fuel or $H_2$. When used as an inert sparging gas, any amount of $H_2$ that is mixed in with the methane provides added value and the methane with $H_2$ can be used without any need for separation. As such, any $H_2$ present adds value to the methane when used as an inert sparging gas.

In a further acceptor-less embodiment, the hydrogen can be removed by running the reaction under partial vacuum. The partial vacuum removes the hydrogen and the higher boiling hydrocarbons participating in the reaction are returned to the reaction medium using a condenser.

In a further acceptor-less embodiment, the reaction is conducted under reflux in an open flask. The hydrogen is swept out of the reaction medium as the reaction refluxes and the reaction proceeds to form alkene product. This embodiment works well with higher boiling alkanes, for example $C_{10}$ and $C_{12}$ alkanes.

In another acceptor-less embodiment, the process comprises providing an alkane feedstock comprising at least one alkane, contacting the alkane with an iridium pincer complex to form an alkene product, and immediately converting the alkene product to a secondary product. The conversion to a secondary product can be an oligomerization, wherein the alkene product is contacted with an oligomerization catalyst. Other reactions to convert the alkene to a secondary product are well known to those of skill in the art. These secondary reactions are also described in US 2013/0090503 "Process for Alkane Oligomerization" filed 12 Sep. 2013, the contents of which are hereby incorporated by reference in their entirety.

Embodiments in which a hydrogen acceptor is utilized are described herein as hydrogen acceptor dehydrogenation reactions. In these embodiments the dehydrogenation reaction is conducted in a closed system and the hydrogen produced reacts with a hydrogen acceptor molecule. The hydrogen acceptors can be ethylene, propene, benzene, and the like, or mixtures thereof. In certain hydrogen acceptor embodiments, the hydrogen acceptors utilized are selected from the group consisting of ethylene, propene, and mixtures thereof. Ethylene, propene, and mixtures thereof are highly abundant light alkenes, readily recyclable, and inexpensive. Propene and ethylene are obtained in abundance as a by-product of oil refining and natural gas processing.

As such, provided are processes utilizing a hydrogen acceptor selected from the group consisting of ethylene, propene, and mixtures thereof. These hydrogen acceptors can be coordinated with the metal center of the iridium pincer complex. The processes using a hydrogen acceptor comprise utilizing ethylene or propene with an iridium pincer complex to dehydrogenate an alkane feedstock.

The alkanes to be dehydrogenated can be $C_4$ to $C_{100}$ alkanes, including for example, pentane, octane, nonane, decane, and dodecane. In certain embodiments, the alkanes to be dehydrogenated are $C_5$ to $C_{100}$ alkanes. The use of iridium pincer complex catalysts disclosed herein has been found to give unprecedented TONs for alkane dehydrogenation both in the gas phase and in the liquid phase. The present processes can show a rate of 100 TON or greater at 10 minutes (based on iridium catalyst) and a turnover frequency (TOF) of 10 min$^{-1}$ or greater. The iridium pincer complex catalysts as disclosed herein also have been found to give unprecedented selectivity to products of the same carbon number as the feed. These selectivies can be 90% or greater or 95% or greater at reasonable conversions of above 50%. In certain instances, the use of iridium pincer complex catalysts also has been found to result in preferential formation of alpha-olefins. For example, gas phase dehydrogenation can result in preferential formation of alpha-olefins.

Among other factors, it has been discovered that the transfer dehydrogenation of alkanes, such as highly abundant light alkanes like butane and pentane, can be accomplished in the gas phase using readily recyclable and cheap hydrogen acceptors with unprecedented turnover numbers (TONs) and selectivities. The hydrogen acceptors are alkenes such as propene and ethylene. It has also been discovered that, in certain instances, the transfer dehydrogenation in the gas phase can provide preferential regioselectivity toward the alpha-olefins, e.g., 1-butene and 1-pentene. Transfer dehydrogenation of higher alkanes such as octane, nonane, decane, and dodecane in the liquid phase with propene or ethylene also has been found to be facile. Overall, the present process provides unprecedented TONs and selectivities for alkane dehydrogenation both in the gas phase and in the liquid phase. Moreover, in certain instances, the reaction results in exceptionally slow isomerization of alpha-olefins, thereby improving desired yields of alpha-olefins. These dehydrogenation reactions are conducted at lower temperatures and thus result in little to no cracking of the alkane feedstock.

The alkane conversion in the present process can be to a variety of alkene products, but primarily to alkene products of the same carbon number as the alkane feedstock. A high selectivity indicates that the alkane is converted primarily to a product of the same carbon number. As such, there is little to no cracking. The conversion can be to an olefin or a diolefin (containing two carbon-carbon double bonds). There can also be a small amount of conversion to a dimer, which is an oligomerization product with a carbon number greater than the alkane feedstock.

As used herein, "selectivity" with regard to the reaction means that an alkane feedstock is converted to an alkene product with the same carbon number. For example, at a selectivity of 90% or greater with a pentane feedstock, 90% or greater of the pentane feedstock is converted to an alkene product with five carbons (e.g., any pentene product). The selectivity indicates that the alkane feedstock and alkene product have the same carbon number. In certain embodiments, the dehydrogenation reaction disclosed herein provides a selectivity of 90% or greater, or 95% or greater, at a reasonable conversion rate of above 50%. The present processes do not yield cracking products since the processes can be conducted at lower temperatures (<260° C.). As such, the processes' selectivities are 90% or greater, or 95% or greater, to alkenes with the same carbon number as the starting alkane.

As used herein, the term "TON" (turnover number) refers to the alkenes produced by a mole of iridium pincer complex before it is inactivated or, alternatively, the hydrogen acceptor consumed by a mole of iridium pincer complex before it is inactivated. Increased TONs are associated with increased conversion. For example, the present processes can show a rate of 100 TON or greater at 10 minutes (based on iridium catalyst) and a turnover frequency (TOF) of 10 $min^{-1}$ or greater. In certain embodiments, the present processes can show a rate of 200 TON or greater at 10 minutes (based on iridium catalyst) and a turnover frequency (TOF) of 20 $min^{-1}$ or greater.

The conversion can be discussed based on the mole or weight % of alkane converted to alkene or the mole or weight % hydrogen acceptor converted to alkane in accepting hydrogen. The hydrogen acceptor embodiments of the present reaction are conducted in a closed system; therefore, the amount of alkane feedstock dehydrogenated to form alkene product is substantially equivalent to the amount of hydrogen acceptor consumed (creating an alkane). The conversion can be in the range of from 10-100%. In the present process, the conversion can be 50% or greater or 75% or greater. In certain embodiments, the conversion can be 95% or greater.

The present processes also can provide for preferential formation of alpha-olefins or 1-alkenes. Regarding the preferential formation of alpha-olefins, the selectivity to the alpha-olefin can be at least 20% of the converted product. In one embodiment, the selectivity to the alpha-olefin can be at least 25% of the converted product. In another embodiment, the selectivity to the alpha-olefin can be at least 30% of the converted product. In yet another embodiment, the selectivity to the alpha-olefin can be at least 50% of the converted product, and can be at least 75% of the converted product. In one embodiment, the selectivity to the alpha-olefin is at least 80% or the converted product and can be at least 85% of the converted product.

Iridium Pincer Complex

As used herein, the term "iridium pincer complex" refers to a complex having a tridentate ligand that is connected to iridium via at least one metal-carbon sigma bond with substituents ortho to this sigma bond being held in a fixed position and coordinating to iridium.

In certain embodiment, the iridium pincer complex can have the following Formula I:

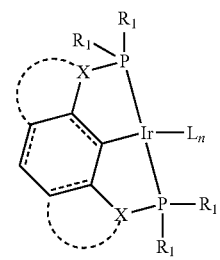

wherein the unspecified optionally fused ring system can be any C—H construction including optional O and N heteroatoms, including non-fused systems and fused ring systems such as naphthalenes;
"n" is an integer from 0 to 4 and each L is independently H, alkyl, or alkene;
each $R_1$ is independently alkyl; and
each X is independently O or $CH_2$.

In certain embodiments, the iridium pincer complex can have the following Formula (Ia):

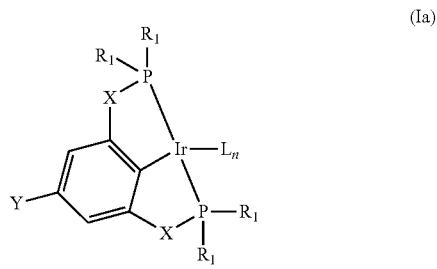

wherein:
"n" is an integer from 0 to 4 and each L is independently H, alkyl, or alkene; each $R_1$ is independently alkyl;
each X is independently O or $CH_2$; and
Y is H or OM wherein M is alkyl, potassium (K), or solid support.

In certain embodiments, the iridium pincer complex can have the following Formula (Ib):

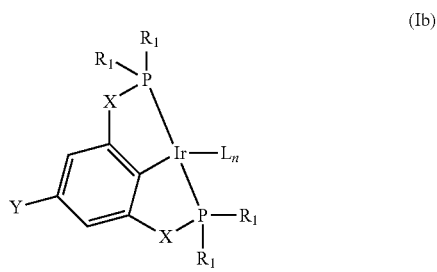

wherein:
"n" is an integer from 0 to 4 and each L is independently H or alkyl;
each $R_1$ is independently alkyl;
each X is independently O or $CH_2$; and
Y is H or OM wherein M is alkyl, K, or solid support.

In certain embodiments, the iridium pincer complex can have the following Formula

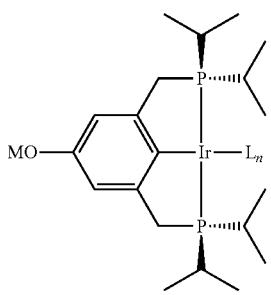

wherein M is K or solid support; "n" is an integer from 0 to 4; and each L is independently H, alkyl, or alkene.

As used herein, in connection with the above Formulae, the term "alkyl" means a branched or straight chain, saturated hydrocarbon radical having 1 to 10 carbons. Exemplary alkyl groups include methyl, ethyl, n-propyl, isopropyl, n-butyl, sec-butyl, isobutyl, tert-butyl, and the like. In certain embodiments, the alkyl has 1 to 5 carbons. In other embodiments, the alkyl has 1 to 4 carbons.

As used herein, in connection with the above Formulae for the iridium pincer complex, the term "alkene" means a branched or straight chain, unsaturated hydrocarbon having 2 to 5 carbons and one carbon-carbon double bond. Exemplary alkene groups include ethylene, propene, but-1-ene, but-2-ene, and 2-methylpropene. In certain embodiments, the alkene has 2 or 3 carbons. In these embodiments, the alkene is ethylene or propene.

The iridium pincer complex can be as described in U.S. Pat. No. 6,982,305 to Nagy, which is incorporated herein by reference in its entirety.

In certain embodiments the iridium pincer complex can also be selected from the group consisting of:

Complex 1

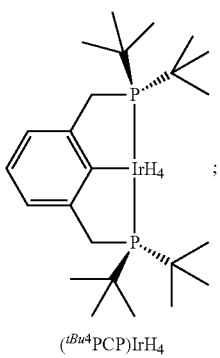

($^{tBu4}$PCP)IrH$_4$

Complex 2

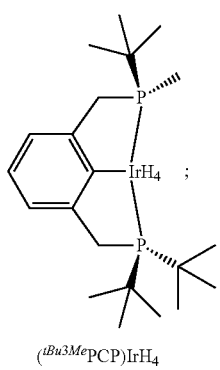

($^{tBu3Me}$PCP)IrH$_4$

Complex 3

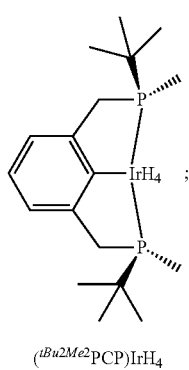

($^{tBu2Me2}$PCP)IrH$_4$

Complex 4

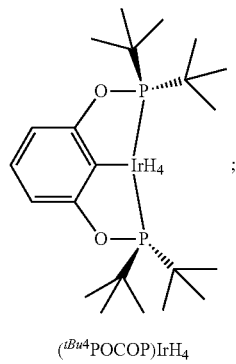

($^{tBu4}$POCOP)IrH$_4$

Complex 5

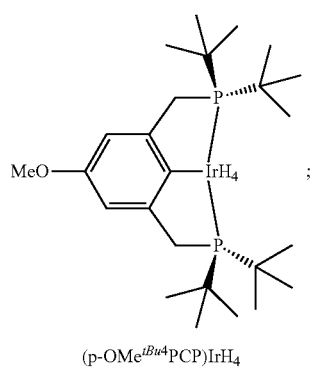

(p-OMe$^{tBu4}$PCP)IrH$_4$

Complex 6

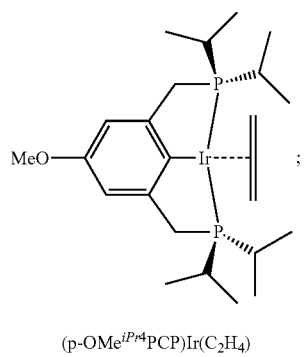

(p-OMe$^{iPr4}$PCP)Ir(C$_2$H$_4$)

Complex 7

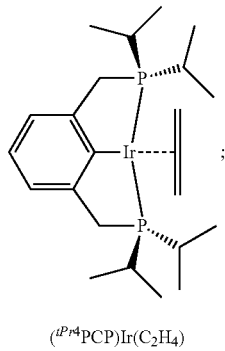

($^{iPr4}$PCP)Ir(C$_2$H$_4$)

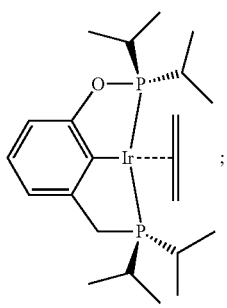

($^{iPr4}$PCOP)Ir(C$_2$H$_4$)

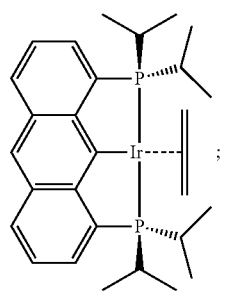

($^{iPr4}$Anthraphos)Ir(C$_2$H$_4$)

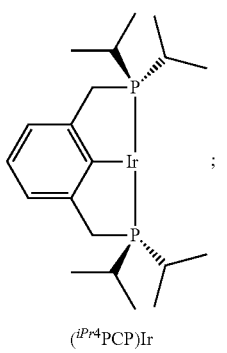

($^{iPr4}$PCP)Ir

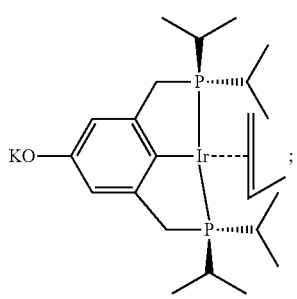

(p-OK—$^{iPr4}$PCP)Ir(C$_3$H$_6$)

Complex 8

Complex 9

Complex 10

Complex 11

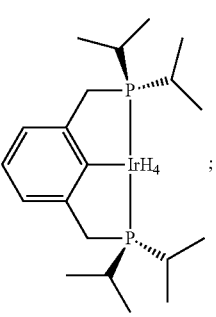

($^{iPr4}$PCP)IrH$_4$

Complex 12 and mixtures thereof.

Certain of the complexes identified herein are novel iridium pincer complexes. For example, Complex 7: ($^{iPr4}$PCP)Ir(C$_2$H$_4$) and Complex 11: (p-OK-$^{iPr4}$PCP)Ir(C$_3$H$_6$) are particularly useful. Complexes 7 and 11 can be unsupported or immobilized on a solid support. In an unsupported embodiment, the complexes can be coated on the glass container in which the dehydrogenation reaction occurs.

The iridium pincer complexes can be a pure solid catalyst compound. The iridium pincer complex can be unsupported or, alternatively, immobilized on a solid support. When supported on solid support, the iridium pincer complex is anchored via a polar anchoring group. The iridium pincer complexes can be supported on any suitable support, such as solid oxides, including but not limited to alumina, silica, titania, magnesia, zirconia, chromia, thoria, boria, beryllia, and mixtures thereof. In certain embodiments, the solid support can be, for example, silica, γ-alumina, basic alumina, florisil, or neutral alumina. In an embodiment, the solid support is florisil or neutral alumina.

In one embodiment of the present processes, the iridium pincer complex utilized is Complex 7: ($^{iPr4}$PCP)Ir(C$_2$H$_4$) or Complex 11: (p-OK-$^{iPr4}$PCP)Ir(C$_3$H$_6$). Complex 7 or Complex 11 can be unsupported or immobilized on a solid support. In a particular embodiment, the iridium pincer complex is Complex 11: (p-OK-$^{iPr4}$PCP)Ir(C$_3$H$_6$) immobilized on a solid support. The solid support can be florisil or neutral alumina. In another embodiment, the iridium pincer complex is Complex 7: ($^{iPr4}$PCP)Ir(C$_2$H$_4$) immobilized on a solid support. The solid support can be florisil or neutral alumina.

When the iridium pincer complex is immobilized on a solid support, it can exhibit unexpected advantages in the dehydrogenation process disclosed herein. In one embodiment, the iridium pincer complex immobilized on a solid support can dehydrogenate an alkane in the presence of a hydrogen acceptor such as ethylene or propene with unprecedented selectivities, rates, and TONs. The supported iridium pincer complex can also exhibit better activity and recyclability in the dehydrogenation process disclosed herein than an unsupported complex.

It has been discovered that the iridium pincer complex immobilized on a solid support can catalyze dehydrogenation at lower temperatures (160° C.-260° C.). with unprecedented TONs and selectivities.

Alkane Feedstock

The alkane feedstock comprises at least one alkane. As used herein, the term "alkane" refers to a branched or straight chain, saturated hydrocarbon having 4 to 100 carbons. Exemplary alkanes include n-butane, isobutane, n-pentane, isopentane, and neopentane. In certain embodiments, the alkane has 5 to 100 carbons. The alkane can be, for example, a butane (e.g. all isomers of butane, including, for example, n-butane, 2-methylpropane, and the like), a pentane (e.g. all isomers of pentane, including, for example, n-pentane, 2-methylbutane, and the like), an octane (e.g. all isomers of octane, including, for example, n-octane, 2,3-dimethylhexane, 4-methylheptane, and the like), or a dodecane (e.g. all isomers of dodecane, including, for example, n-dodecane, 2-methyl-3-methyldecane, 3-ethyldecane, and the like). In an embodiment, the alkane comprises a butane. In another embodiment, the alkane comprises a pentane. In yet another embodiment, the alkane comprises an octane. In another embodiment, the alkane comprises a dodecane. In an embodiment, the alkane is selected from the group consisting of a butane, a pentane, an octane, a nonane, a decane, a dodecane, and mixtures thereof. In certain embodiments, the alkane is a straight chain alkane.

The alkane feedstock can comprise a single alkane or a mixture of alkanes. As such, the alkane to be dehydrogenated can be a single alkane or a mixture of alkanes. The alkane can be a mixture of isomers of an alkane of a single carbon number. The alkane feedstock can comprise hydrocarbons in addition to the alkane or mixture of alkanes to be dehydrogenated. A hydrocarbon feed composition from any suitable source can be used as the alkane feedstock. Alternatively, the alkane feedstock can be isolated from a hydrocarbon feed composition in accordance with known techniques such as fractional distillation, cracking, reforming, dehydrogenation, etc. (including combinations thereof). For example, n-paraffin as a feed can be obtained by either by adsorption or extractive crystallization. One suitable source of the alkane feedstock described further herein, by no means to be taken as limiting, is the output of a Fischer-Tropsch reaction system.

The production of hydrocarbon compositions comprising alkanes from synthesis gas by Fischer-Tropsch catalysis is well known and can be carried out in accordance with known techniques by reaction of a synthesis gas in the presence of Fischer-Tropsch catalyst in a reactor. Any suitable catalyst can be used, including but not limited to iron and cobalt catalysts. See, e.g., U.S. Pat. No. 6,217,830 to Roberts and Kilpatrick; see also U.S. Pat. Nos. 6,880,635; 6,838,487; 6,201,030; 6,068,760; 5,821,270; 5,817,701; 5,811,363; 5,620,676; and 2,620,347.

The production of synthesis gas from carbonaceous or organic materials, such as coal (including coal fines), natural gas, methane, refinery bottoms, vegetative materials such as wood or other biomass, and combinations thereof, is well known and can be carried out in accordance with known techniques. In some embodiments such production involves the partial oxidation of the carbonaceous or organic material at elevated temperatures, and optionally elevated pressures, with a limited volume of oxygen. The reaction is preferably carried out in a reactor into which the material is fed, together with additional agents such as steam, carbon dioxide, or various other materials. See e.g., U.S. Pat. No. 4,959,080; see also U.S. Pat. No. 4,805,561.

Alkene Product

The alkene product comprises at least one alkene. As used herein, in connection with the alkene product, the term "alkene" refers to a branched or straight chain, unsaturated hydrocarbon having 4 to 100 carbons and one or more carbon-carbon double bonds. In certain embodiments the alkene product comprises 5 to 100 carbons. In certain embodiments the alkene product comprises 4 to 100 carbons and one or two double bonds. In other embodiments, the alkene has 5 to 100 carbons and one or two double bonds. In yet other embodiments, the alkene has 4 to 100 carbons and one double bond. In certain other embodiments, the alkene has 5 to 100 carbons and one double bond. The alkene can be, for example, a butene (e.g., all isomers of butene, including, for example, 1-butene, 2-butene, 2-methyl-1-propene, and the like), a pentene (e.g., all isomers of pentene, including, for example, 1-pentene, 2-pentene, and the like), an octene (e.g., all isomers of octene, including, for example, 1-octene, 2-octene, 2-methyl-3-heptene, and the like), or a dodecene (e.g., all isomers of dodecene, including, for example, 1-dodecene, 2-dodecene, 2-methyl-3-undecene, and the like). In an embodiment, the alkene comprises a butene. In another embodiment, the alkene comprises a pentene. In yet another embodiment, the alkene comprises an octene. In another embodiment, the alkene comprises a dodecene. In an embodiment, the alkene is selected from the group consisting of a butene, a pentene, an octene, a nonene, a decene, a dodecene, and mixtures thereof.

One advantage of the present processes is high selectivity and yield to the same carbon number product as the feed since no cracked products are formed at the low reaction temperatures. Another advantage is the ability to produce odd-carbon number alkene products. In the present processes, the alkane feedstock is converted to an alkene product with the same carbon number. For example, at a selectivity of 90% or greater with a pentane feedstock, 90% or greater of the pentane feedstock is converted to an alkene product with five carbons (e.g., any pentene product). In certain embodiments, the dehydrogenation reaction disclosed herein provides a selectivity of 90% or greater, or 95% or greater, at a reasonable conversion rate of above 50%.

Primarily, the alkene is the same carbon number as the feed. The alkene can comprise a single alkene or a mixture of alkenes. The alkene can be a mixture of isomers of an alkene of a single carbon number. The alkene can have a double bond at the primary position (e.g., 1-butene, 1-pentene, 1-octene, 1-dodecene) such that the alkene is an alpha-olefin.

The alkene product can contain an alkene with one double bond, a diene (i.e., an alkene with two carbon-carbon double bonds), a dimer, and mixtures thereof.

Reaction Conditions

In general, the dehydrogenation reaction can be run under conventional dehydrogenation reaction conditions. However, the iridium pincer complexes disclosed herein do not require high temperatures or pressures. Therefore, the reaction can be run at a reaction temperature less than 300° C. Higher temperatures up to 400° C. or 500° C. or higher can be used, but are not necessary and are not desired. Suitable temperatures include, for example, a temperature in the range of 160° C.-260° C. In certain embodiments a temperature in the range of 200° C.-260° C. can be utilized. In other embodiments, a temperature in the range of 225° C.-250° C. can be utilized. In yet other embodiments a temperature in the range of 240° C.-250° C. can be utilized. In an embodiment, a temperature of about 240° C. is used, which temperature is sufficient to maintain ethylene or propylene in the gaseous phase. In another embodiment, a temperature of about 200° C. is used. In yet another embodiment, a temperature of about 160° C. is used. The pressure is adjusted accordingly.

Conducting the dehydrogenation reaction at temperatures of less than 300° C. (e.g., 160° C.-260° C.), results in extremely little to no cracking of the alkane feedstock. Accordingly, the present dehydrogenation reactions can be run with unprecedented selectivities.

The length of reaction time with best results for selectivity varies based upon the catalyst. The reaction time is generally in the range of from about 1 minute or less (e.g., about 30 seconds) up to 24 hours. The reaction time can be up to about 10 minutes, up to about 40 minutes, up to about 80 minutes, up to about 100 minutes, up to about 180 minutes, or up to about 600 minutes. The reaction time can be about 10 minutes, about 40 minutes, about 80 minutes, about 100 minutes, about 180 minutes, or about 600 minutes. In one embodiment, the reaction time is from about 10-100 minutes. Alternatively, the reaction time can be from about 10-180 minutes. In another embodiment, the reaction time can be from about 20-180 minutes. In another embodiment, the reaction time can be from about 40-100 minutes. In yet another embodiment, the reaction time can be from about 40-180 minutes. The reaction time can be from about 10-40 minutes, about 10-80 minutes, about 10-100 minutes, about 10-180 minutes, or about 10-600 minutes.

In an embodiment, the reaction takes place in the presence of a solid catalyst and a gaseous hydrogen acceptor and a gaseous or liquid alkane. The use of a solid catalyst also works well with a gaseous phase for the alkane and for the hydrogen acceptor. A liquid phase can also be used for the reaction. While a gas phase system or liquid phase system can be used, as discussed, a three phase system of solid-liquid-gas can also be successful. In a three phase system, the catalyst can be a solid; the hydrogen acceptor can be gaseous; and the alkane can be liquid.

As used herein, the term "gas phase" refers to the alkane and the hydrogen acceptor both being gaseous during the dehydrogenation reaction. However, during the "gas phase" reaction, the catalyst can be solid, liquid, or gas. In an embodiment, the reaction is conducted under supercritical conditions.

As used herein, the term "liquid phase" refers to the alkane and the hydrogen acceptor both being liquid during the dehydrogenation reaction. However, during the "liquid phase" reaction the catalyst can be solid, liquid, or gas.

The reaction can be run with varied catalyst configurations. For example, the reaction is run in a stirred reactor in one embodiment. The reaction can also be run in a fixed bed or fluidized bed reactor. The reactor can be a packed-bed reactor, trickle-bed reactor, bubble-column reactor, ebullating-bed reactor, and the like. The system to be run, whether gas, liquid, or three phase, helps to determine the catalyst configuration and type of reactor to be used. The reaction choice is based on a fundamental characterization of the reaction.

For example, when using sparging to remove hydrogen, a continuous stirred tank reactor can be used. Bubble column reactors can also be utilized to conduct gas-liquid reactions. A fixed bed reactor with a supported iridium pincer complex can be utilized with counter-current flow of a stripping gas (e.g., Ar).

The following examples are provided to better illustrate the process disclosed herein. The examples are meant to be solely illustrative, and not limiting.

EXAMPLES

As demonstrated in Examples 1 and 2 below, it has been found that iridium pincer complex catalyzed dehydrogenation of pentane with propene or ethylene at temperatures below 300° C., for example 240° C., results in reactions occurring in the gas phase. In Examples 1 and 2, pentane containing catalytic amounts of iridium pincer complex catalysts was subjected to low temperatures under propene or ethylene atmosphere in sealed vials with large head space. In many cases, such conditions resulted in the iridium pincer complex catalysts splashing off to coat the glass surface leading to very high activity and nearly full consumption of the gaseous acceptors.

In the gas phase transfer dehydrogenation of pentane with propene as the hydrogen acceptor of Example 1, while Complex 7: $(^{iPr4}PCP)Ir(C_2H_4)$ gave very good rates and conversion, the conversion was also high with Complex 3: $(^{tBu2Me2}PCP)IrH_4$. On the other hand, in an analogous gas phase reaction with ethylene as the hydrogen acceptor of Example 2, Complex 7: $(^{iPr4}PCP)Ir(C_2H_4)$ not only showed a high rate but also resulted in excellent conversion. Further, with ethylene as acceptor, Complex 7: $(^{iPr4}PCP)Ir(C_2H_4)$ showed exceptional preference toward formation of 1-pentene. Interestingly, this selectivity observed in the gas phase does not substantially decrease and remains almost the same at longer reaction times.

Example 1: Dehydrogenation of n-Pentane with Propene

In a typical experimental set up, a 100 µl stock solution of n-pentane containing 1 mM iridium pincer complex catalyst was taken in a few custom made thick walled 1.5 ml vials inside a glove box. The vials were then connected to Kontes adapter via tygon tubings and degassed in a high vacuum line. One atmosphere of propene was then introduced to the system and the kontes valves were sealed. The contents of the vials were frozen in liquid nitrogen and the vials were flame sealed. Note that one atm propene charged in a 3 ml space condenses to a 1.5 ml vial space upon flame sealing rendering the amount of propene in each vial to be about 2 atm. The vials were then placed in a pre heated aluminum block inside a gas chromatography (GC) oven maintained at 240° C. and subjected to interval free heating for a stipulated time. The GC oven was then cooled to room temperature, the vials were taken out, the contents were frozen in liquid nitrogen and the tubes were broken open. The contents of each vial were analyzed by GC.

The vapor pressure of n-pentane at 240° C. is calculated to be 52 atm. A pentane stock solution (100 µl) in each of these 1.5 ml vials can generate about 24 atm if all of the pentane goes to the gas phase at 240° C. The transfer dehydrogenation of n-pentane with propene in these vials is essentially in the gas phase.

TABLE 1

Dehydrogenation of n-pentane catalyzed by pincer iridium complexes at propene pressure of 2 atm ("1.2 M") at 240° C.

| Entry | Catalyst 1 mM | Time (min) | 1-Pentene mM | Trans-2-Pentene mM | Cis-2-Pentene mM | 1,3-pentadienes mM | Total Olefins mM | propene consumed mM % | 1-pentene Selectivity % |
|---|---|---|---|---|---|---|---|---|---|
| 1[a] | Complex 1 | 10 | 15 | 3 | 2 | — | 20 | 20 2% | 75 |
|  |  | 40 | 17 | 2 | 1 | — | 20 | 20 2% | 85 |
|  |  | 180 | ND | ND | ND | ND | ND | ND | ND |
| 2[b] | Complex 5 | 10 | 18 | 3 | 1 | 1 | 23 | 24 2% | 75 |
|  |  | 40 | ND | ND | ND | ND | ND | ND | ND |
|  |  | 180 | 20 | 3 | 1 | 1 | 25 | 26 2% | 77 |
| 3[b] | Complex 2 | 10 | 0 | 0 | 0 | 0 | 0 | 0 | 0 |
|  |  | 40 | 50 | 9 | 0 | 0 | 59 | 59 5% | 85 |
|  |  | 180 | 36 | 8 | 1 | 0 | 45 | 45 4% | 80 |
| 4[a] | Complex 3 | 10 | 113 | 140 | 63 | 25 | 341 | 366 30% | 33 |
|  |  | 40 | 152 | 210 | 95 | 43 | 500 | 543 44% | 30 |
|  |  | 180 | 195 ± 14 | 409 ± 25 | 194 ± 16 | 148 ± 14 | 945 ± 65 | 1093 95% | 21 |
| 5[a] | Complex 7 | 10 | 143 ± 7 | 312 ± 9 | 140 ± 5 | 40 ± 1 | 634 ± 22 | 674 55% | 21 |
|  |  | 40 | 170 ± 6 | 422 ± 4 | 188 ± 2 | 70 ± 0 | 850 ± 1 | 920 75% | 18 |
|  |  | 180 | 226 ± 14 | 493 ± 11 | 226 ± 9 | 108 ± 7 | 1054 ± 13 | 1162 95% | 19 |
| 6[b] | Complex 6 | 10 | 116 ± 11 | 34 ± 6 | 16 ± 2 | 3 | 169 ± 19 | 172 ± 19 13% | 67 |
|  |  | 40 | 207 | 81 | 39 | 9 | 336 | 345 28% | 60 |
|  |  | 180 | 183 | 80 | 38 | 10 | 311 | 321 25% | 57 |
| 7[a] | Complex 8 | 10 | 69 ± 9 | 50 ± 1 | 19 | 3 | 141 ± 11 | 144 ± 11 11% | 48 |
|  |  | 40 | 119 | 145 | 50 | 14 | 328 | 342 28% | 36 |
|  |  | 180 | 168 | 250 | 82 | 21 | 521 | 543 44% | 32 |
| 8[a] | Complex 9 | 10 | 79 | 27 | 4 | 2 | 112 | 114 9% | 69 |
|  |  | 40 | 90 | 33 | 6 | 2 | 131 | 133 11% | 68 |
|  |  | 180 | 100 | 49 | 8 | 4 | 161 | 165 13% | 61 |
| 9[b] | Complex 4 | 10 | 0 | 0 | 0 | 0 | 0 | 0 | 0 |
|  |  | 40 | 0 | 0 | 0 | 0 | 0 | 0 | 0 |
|  |  | 180 | 4 | 3 | 1 | — | 8 | 8 1% | 50 |

Reaction conditions; 1 mM pincer iridium catalysts in neat pentane [8.7 M] under 2 atm propene "[1.2 M]" at 240° C., [a]These catalysts are found to coat the glass surface, [b]These catalysts form insoluble residues at the bottom of the vial after the reaction The transfer dehydrogenation of n-pentane was first tested with Complex 1: $(^{tBu4}PCP)IrH_4$ and its p-methoxy derivative parent iridium pincer complex Complex 5: (p-ome$^{tBu4}$PCP)IrH$_4$. These catalysts showed good selectivity toward 1-pentene but quite surprisingly, the selectivity remained almost the same at longer reaction times (Entries 1 and 2, Table 1). The runs were repeated for additional iridium pincer complexes, under the same conditions, with the results shown in Table 1.

Complex 2: $(^{tBu3Me}PCP)IrH_4$ where one of the t-Bu groups is substituted with a Me group showed a negligible improvement in catalytic activity (Entry 3, Table 1). However, high selectivity toward 1-pentene was uniformly observed at all times. Substitution of the second t-Bu group by a Me group as in Complex 3: $(^{tBu2Me2}PCP)IrH_4$ showed a drastic increase in the rate and conversion of the reaction. After 180 minutes the amount of pentenes formed corresponded to consumption of almost 95% of the propene. These reactions were less selective toward 1-pentene showing a selectivity of only 33% and 21% after 10 and 180 minutes respectively.

In general, for the iridium pincer complex catalyzed transfer dehydrogenation of pentane with propene, it was believed that the catalyst would be present as a solid mass at the bottom of the vessel when all substrates are in the gas phase at 240° C. As such, it was generally believed that one would encounter substrate mixing problems and hence low conversions. Hence, the high conversions obtained in the propene reactions with Complex 3: $(^{tBu2Me2}PCP)IrH_4$ as the catalyst were quite surprising and rationally challenging. At this stage, it was observed that in the reactions with Complex 2: $(^{tBu3Me}PCP)IrH_4$, vials obtained after heating at 240° C. at various times contained insoluble residues at the bottom and a clear colorless pentane/pentene mixture (Entry 3, Table 1). On the other hand, in the case of reactions with Complex 3: $(^{tBu2Me2}PCP)IrH_4$, the vials obtained after heating at 240° C. at all times had a clear orange colored solution. In one of runs for the reaction with Complex 3: $(^{tBu2Me2}PCP)IrH_4$ the GC oven was cooled to 60° C. from 240° C. and slowly opened taking all the safety precautions. At this stage the top portion of the vial was cool and the base was still hot as it was placed inside the aluminum block. A video of the vial recorded at this juncture clearly showed bright red droplets formed at various positions at the topmost portions of the vial. As the vial cooled, the red droplets condensed into the solution. One explanation is that at temperatures as high as 240° C., the catalyst either vaporizes and migrates to the top of the vial or is splashed off to the sides by the sudden vaporization of the liquid essentially coating the glass during the process. As the vial cools, the pentane washes the catalyst from the glass resulting in bright red droplets which condense as an orange colored solution.

Independent tests were performed under identical conditions but in the absence of pentane to investigate the possibility of vaporization of pincer catalysts. These tests indicated that the iridium pincer complex catalysts neither migrated to the top nor coated the glass surface when heated at 240° C. under propene atmosphere. Hence, it is likely that when a pentane solution containing iridium pincer complex catalyst is heated at 240° C., the catalysts are splashed off to the sides of the vessel and depending on the morphology of the catalyst, it either prefers to stick to the glass surface or fall off. In many instances, the catalysts which were observed to coat the glass showed good activity.

When Complex 7: $(^{iPr4}PCP)Ir(C_2H_4)$ was used for the transfer dehydrogenation of pentane under 2 atm of propene, the catalyst was found to coat the glass. The dehydrogenation catalyzed by Complex 7: $(^{iPr4}PCP)Ir(C_2H_4)$ proceeded at twice the rate observed with Complex 3 but with comparable conversion (Entry 5, Table 1) albeit with low selectivity. However, its p-methoxy-derivative Complex 6: (p-OMe$^{iPr4}$PCP)Ir(C$_2$H$_4$) showed a slower rate and low conversion (Entry 6, Table 1). The reaction also exhibited high selectivity toward 1-pentene at all times and the reaction leveled off after 40 minutes. This catalyst does not coat the glass and the catalyst forms insoluble residue upon heating under propene atmosphere.

Complex 8: $(^{iPr4}PCOP)Ir(C_2H_4)$ showed a similar behavior as Complex 3: $(^{tBu2Me2}PCP)IrH_4$ and Complex 7: $(^{iPr4}PCP)Ir(C_2H_4)$ by coating the glass. The activity of this catalyst was good (Entry 7, Table 1) but less than that of either Complex 3 or Complex 7, though the selectivity toward 1-pentene was slightly higher compared to Complex 3 or Complex 7. Though Complex 9: $(^{iPr4}Anthraphos)Ir(C_2H_4)$ was observed to coat the glass, its activity was surprisingly not as good as expected (Entry 8, Table 1).

In an attempt to increase the amount of dehydrogenated products, the reaction was performed under 4 atm propene ["2.5 M"] using Complex 7: $(^{iPr4}PCP)Ir(C_2H_4)$ as the catalyst at 240° C. The reaction showed a high rate of 1350 turnovers after 10 minutes with 30% selectivity toward 1-pentene. No appreciable improvement in conversion at longer times was observed.

It was discovered with regard to this pentane and propene chemistry that the use of cheap hydrogen acceptors for light alkane dehydrogenation was quite viable. In contrast to normal expectations, almost uniform selectivity at all times is observed. In the propene reactions, catalyst that gave excellent selectivity toward alpha-olefins resulted in low conversions and those that gave rise to high TONs were less selective.

Example 2: Dehydrogenation of n-Pentane with Ethylene

The transfer dehydrogenation of pentane with ethylene as acceptor was attempted using a few selected catalysts (Complexes 3, 6, 7, 8 and 9) that demonstrated acceptable activity in the propene reactions. The transfer dehydrogenation of pentane with ethylene catalyzed by Complex 3: $(^{tBu2Me2}PCP)Ir(H_4)$ proceeded at a rate of about 100 turnovers in 10 minutes with a selectivity of about 70% toward 1-pentene (Entry1, Table 2). After 180 minutes the conversion was about 261 turnovers and the selectivity had dropped to 50%. The selectivity at initial times is almost the same but as the reaction goes from 40 minutes to 180 minutes, the drop in selectivity is about 20% (Entry 1, Table 2). This drop in selectivity is more pronounced than in the propene reactions catalyzed by Complex 3: $(^{tBu2Me2}PCP)IrH_4$ (10% drop, Entry 4, Table 1). Upon comparing the pentane dehydrogenation with either propene or ethylene catalyzed by Complex 3: $(^{tBu2Me2}PCP)IrH_4$, it is apparent that the selectivity toward 1-pentene is slightly higher with ethylene as the acceptor. The best comparison would be the 10 minutes run (360 TON, 30% selectivity) for propene reactions in Table 1 (Entry 4) and the 180 minutes run (260 TON, 50% selectivity) for ethylene reactions in Table 2 (Entry 1).

Analogous reaction catalyzed by Complex 7: $(^{iPr4}PCP)Ir(C_2H_4)$ showed rates comparable to Complex 3: $(^{tBu2Me2}PCP)IrH_4$ but with excellent selectivity. Comparison of the regioselectivities of Complex 7 and Complex 3 under identical TONs (10 and 180 minutes of Entry 1 with 10 and 40 minutes of Entry 2) was indicative of the excellent regioselectivity of Complex 7: $(^{iPr4}PCP)Ir(C_2H_4)$ compared to Complex 3: $(^{tBu2Me2}PCP)IrH_4$. Further, Complex 7: $(^{iPr4}PCP)Ir(C_2H_4)$ exhibited very high conversion compared to Complex 3 or any other catalysts screened in Table 2. It is also noteworthy that Complex 7: $(^{iPr4}PCP)Ir(C_2H_4)$ catalyzed pentane dehydrogenation with ethylene exhibited higher regioselectivity than the analogous reaction with propene as acceptor under comparable TONs. While 21% selectivity toward 1-pentene is observed after 10 minutes with propene as acceptor (670 TON, Entry 5, Table 1), use of ethylene gives a regioselectivity of 65% after 100 minutes (680 TON, Entry 2, Table 2).

The rest of catalysts Complex 6: (p-OMe$^{iPr4}$PCP)Ir(C$_2$H$_4$), Complex 8: $(^{iPr4}PCOP)Ir(C_2H_4)$ and Complex 9: $(^{iPr4}Anthraphos)Ir(C_2H_4)$ that were screened for pentane dehydrogenation with ethylene as acceptors (Entries 3, 4 and 5) though exhibited selectivities higher than the corresponding reactions with propene as acceptors in Table 1, the catalytic activity was not appreciable. Note that all reactions studied in Tables 1 and 2 resulted in catalyst splashing off and coating the glass. These studies indicate that though coating the glass is essential to counter the substrate mixing problem, the activity depends on the nature of the catalyst. For instance, Complex 3: $(^{tBu2Me2}PCP)IrH_4$ coated the glass in pentane dehydrogenation reactions with both propene and ethylene as acceptor; however, the catalytic activity was exceptional only in the case of propene as acceptor. With ethylene as acceptor though Complex 3: $(^{tBu2Me2}PCP)IrH_4$ exhibited a high rate, the conversion after 180 minutes was low. The results are shown in Table 2.

TABLE 2

Dehydrogenation of n-pentane catalyzed by pincer iridium complexes at propene pressure of 2 atm ("1.2 M") at 240° C.

| Entry | Catalyst 1 mM | Time (min) | 1-Pentene mM | Trans-2-Pentene mM | Cis-2-Pentene mM | 1,3-pentadienes mM | Total Olefins mM | propene consumed mM % | 1-pentene Selectivity % |
|---|---|---|---|---|---|---|---|---|---|
| 1 | Complex 3 | 10 | 70 ± 3 | 18 ± 2 | 8 ± 1 | 1 ± 0 | 98 ± 6 | 98 8% | 71 |
|  |  | 40 | 90 | 29 | 12 | 2 | 133 | 135 11% | 70 |
|  |  | 180 | 135 | 79 | 33 | 7 | 254 | 261 21% | 52 |
| 2 | Complex 7 | 10 | 60 ± 0 | 7 ± 2 | 3 ± 1 | 2 ± 1 | 72 ± 5 | 75 6% | 83 |
|  |  | 40 | 251 | 44 | 22 | 5 | 322 | 327 27% | 78 |
|  |  | 100 | 427 | 135 | 70 | 28 | 660 | 688 56% | 65 |
|  |  | 180 | 419 | 176 | 88 | 41 | 724 | 765 62% | 58 |

TABLE 2-continued

Dehydrogenation of n-pentane catalyzed by pincer iridium complexes at propene pressure of 2 atm ("1.2 M") at 240° C.

| Entry | Catalyst 1 mM | Time (min) | 1-Pentene mM | Trans-2-Pentene mM | Cis-2-Pentene mM | 1,3-pentadienes mM | Total Olefins mM | propene consumed mM % | 1-pentene Selectivity % |
|---|---|---|---|---|---|---|---|---|---|
| 3 | Complex 6 | 10 | 36 | 3 | 2 | — | 41 | 41 3% | 88 |
|  |  | 40 | 66 | 10 | 4 | — | 80 | 80 6% | 83 |
|  |  | 180 | 120 | 23 | 11 | 2 | 156 | 158 13% | 77 |
| 4 | Complex 8 | 10 | 12 | 3 | 2 | — | 17 | 17 1% | 71 |
|  |  | 40 | 34 | 7 | 4 | — | 45 | 45 4% | 76 |
|  |  | 180 | ND | ND | ND | ND | ND | ND | ND |
| 5 | Complex 9 | 10 | 10 | 36 | 4 | — | 41 | 41 3% | 88 |
|  |  | 40 | 40 | 46 | 5 | — | 53 | 53 4% | 87 |
|  |  | 180 | 180 | 118 | 28 | 1 | 152 | 153 12% | 77 |

Example 3: Dehydrogenation of n-Octane with Propene

As demonstrated in Examples 3 and 4, transfer dehydrogenation of higher alkanes such as octane and dodecane in the liquid phase with either propene or ethylene has been found to be facile. In Example 3, Complex 7: ($^{iPr4}$PCP)Ir(C$_2$H$_4$) was found to be the most efficient catalyst with both propene and ethylene as acceptors.

Example 3 can be viewed as demonstrating exceptional selectivity of iridium pincer complex catalyzed transfer dehydrogenation reactions toward alpha-olefins when the reaction is performed in the liquid phase. This example can also be viewed as demonstrating high turnover numbers for iridium complex catalyzed transfer dehydrogenation performed in the liquid phase. This example can further be viewed as demonstrating octane transfer dehydrogenation rapidly occurs using ethylene or propene as a hydrogen acceptor where the reaction is essentially in the liquid phase. Octane was used in the same glass vials under similar ethylene or propene pressures as discussed for the pentane reactions.

The vapor pressure of n-octane at 240° C. is calculated to be 11 atm. A octane stock solution (100 µl) in each of these 1.5 ml vials produces about 17 atm if all of the octane would vaporize. Therefore, the transfer dehydrogenation of octane with propene in these vials is essentially in the liquid phase.

The transfer dehydrogenation of octane was first tested at 240° C. with 1 mM Complex 7: ($^{iPr4}$PCP)Ir(C$_2$H$_4$) at a propene pressure of 2 atm. With 2 atm propene in a 1.5 ml vial, one has a concentration of about "1.2 M" propene if all of the hydrogen acceptor were to be in solution. Complex 7: ($^{iPr4}$PCP)Ir(C$_2$H$_4$) was highly active for this reaction giving 449 TON after 10 minutes and reaching 1156 TON after 180 minutes indicating that most of the propene has been consumed at this stage (Entry 1, Table 3). The reaction occurring in the liquid phase permitted increase of propene pressures to probe for higher TONs. Increasing propene pressure had a favorable effect on the rates and conversion. At a propene pressure of 6.5 atm, a rate as high as 1756 TON was obtained with a conversion of 2651 TON (2651 TON of total olefins using 1 mM ($^{iPr4}$PCP)Ir(C$_2$H$_4$) as catalyst). Runs were made using various catalysts and various propene pressures. The runs and their results are detailed in Table 3.

TABLE 3

Dehydrogenation of n-octane catalyzed by pincer iridium complexes under various propene pressures at 240° C.

| Entry | Catalyst 1 mM | Propene P "M" | Time min | Monoenes mM 1-octene | Monoenes mM Total | Dienes mM | Higher fractions mM | Total Olefins mM | propene consumed mM % | 1-octene Selectivity % |
|---|---|---|---|---|---|---|---|---|---|---|
| 1 | Complex 7 | 2 atm "1.2M" | 10 | 160 | 405 | 38 | 6 | 449 | 400 41% | 36 |
|  |  |  | 40 | 175 | 724 | 124 | 18 | 866 | 1026 84% | 20 |
|  |  |  | 180 | 210 ± 86 | 983 ± 150 | 166 ± 29 | 36 ± 2 | 1156 ± 119 | 1364 111% | 18 |
| 2[a] | Complex 7 | 3.5 atm "2.1M" | 10 | 155 | 897 | 183 | 50 | 1130 | 1413 66% | 14 |
|  |  |  | 40 | 190 | 1080 | 222 | 63 | 1365 | 1713 78% | 14 |
|  |  |  | 180 | 164 | 1190 | 273 | 100 | 1563 | 2036 95% | 10 |
| 3[a] | Complex 7 | 6.5 atm "4.0M" | 10 | 242 ± 20 | 1393 ± 45 | 232 ± 93 | 131 ± 34 | 1756 ± 172 | 2250 56% | 14 |
|  |  |  | 40 | 198 | 1577 | 468 | 351 | 2396 | 3566 89% | 8 |
|  |  |  | 180 | 219 | 1706 | 535 | 410 | 2651 | 4006 100% | 8 |
| 4[b] | Complex 3 | 6.5 atm "4.0M" | 10 | 68 ± 4 | 204 ± 20 | 2 ± 1 | 1 | 206 ± 32 | 278 7% | 33 |
|  |  |  | 40 | 143 | 972 | 140 | 60 | 1172 | 1432 36% | 12 |
|  |  |  | 180 | 148 | 959 | 126 | 39 | 1124 | 1328 33% | 13 |
| 5[a] | Complex 6 | 6.5 atm "4.0M" | 10 | 198 | 671 | 31 | 6 | 708 | 751 19% | 28 |
|  |  |  | 40 | 259 | 1022 | 89 | 33 | 1144 | 1299 32% | 22 |
|  |  |  | 180 | 253 | 940 | 70 | 18 | 1028 | 1134 28% | 25 |
| 6[a] | Complex 8 | 6.5 atm "4.0M" | 10 | 81 | 296 | 12 | 1 | 309 | 323 8% | 26 |
|  |  |  | 40 | 137 | 558 | 39 | 7 | 604 | 657 16% | 23 |
|  |  |  | 180 | 151 | 560 | 48 | 3 | 611 | 665 17% | 24 |

TABLE 3-continued

Dehydrogenation of n-octane catalyzed by pincer iridium complexes under various propene pressures at 240° C.

| Entry | Catalyst 1 mM | Propene P "M" | Time min | Monoenes mM 1-octene | Monoenes mM Total | Dienes mM | Higher fractions mM | Total Olefins mM | propene consumed mM % | 1-octene Selectivity % |
|---|---|---|---|---|---|---|---|---|---|---|
| 7[b] | Complex 9 | 6.5 atm "4.0M" | 10 | 248 | 1132 | 97 | 25 | 1254 | 1401 35% | 20 |
|  |  |  | 40 | 276 ± 4 | 1268 ± 82 | 109 ± 23 | 21 ± 12 | 1398 | 1549 39% | 20 |
|  |  |  | 180 | 277 | 1091 | 82 | 21 | 1194 | 1318 33% | 23 |

Reaction conditions; 1 mM pincer iridium catalysts in neat pentane [8.7 M] under 2 atm propene "[1.2 M]", [a]These catalyst form insoluble residues at the bottom of the vial after the reaction, [b]These catalysts are found to vaporize and coat the glass surface The dehydrogenation of n-octane over selected iridium pincer complexes under ethylene pressure of 6.5 atm at 240° C. was demonstrated. Results and details of the runs are shown in Table 4.

TABLE 4

Dehydrogenation of n-octane catalyzed by pincer iridium complexes at ethylene pressure of 6.5 atm ("4.0 M") at 240° C.

| Entry | Catalyst 1 mM | Time min | Monoenes mM 1-octene | Monoenes mM Total | Dienes mM | Higher fractions mM | Total Olefins mM | propene consumed mM % | 1-octene Selectivity % |
|---|---|---|---|---|---|---|---|---|---|
| 1[a] | Complex 7 | 10 | 200 | 506 | 17 | 4 | 527 | 552 14% | 38 |
|  |  | 40 | ND | ND | ND | ND | ND | ND | ND |
|  |  | 180 | 377 | 1224 | 64 | 17 | 1305 | 1403 35% | 29 |
| 2[b] | Complex 9 | 10 | 172 | 319 | 2 | — | 321 | 323 8% | 54 |
|  |  | 40 | 229 | 492 | 5 | 1 | 498 | 505 13% | 46 |
|  |  | 180 | 251 | 771 | 22 | 1 | 794 | 818 20% | 32 |
| 3[a] | Complex 3 | 10 | 103 | 388 | 16 | 2 | 406 | 424 11% | 25 |
|  |  | 40 | 126 | 517 | 28 | 6 | 551 | 585 15% | 23 |
|  |  | 180 | 127 | 505 | 28 | 6 | 539 | 573 14% | 24 |
| 4[a] | Complex 6 | 10 | 25 | 36 | 1 | — | 37 | 38 1% | 68 |
|  |  | 40 | 114 | 178 | 1 | — | 179 | 180 4% | 64 |
|  |  | 180 | ND | ND | ND | ND | ND | ND | ND |
| 5[b] | Complex 8 | 10 | 47 | 92 | 1 | — | 93 | 94 2% | 50 |
|  |  | 40 | 49 | 88 | 1 | — | 89 | 90 2% | 55 |
|  |  | 180 | ND | ND | ND | ND | ND | ND | ND |

Reaction conditions; 1 mM pincer iridium catalysts in neat pentane [8.7 M] under 6.5 atm ethylene "[6.5 M]"

Example 4: Dehydrogenation of n-Dodecane with Ethylene

N-dodecane was dehydrogenated using ethylene as the hydrogen acceptor. The details of the reaction and the results of the runs are set forth in Table 5. This example can be viewed as demonstrating high turnover numbers for iridium complex catalyzed transfer dehydrogenation performed in the liquid phase. This example can also be viewed as demonstrating dodecane transfer dehydrogenation rapidly occurs using ethylene as a hydrogen acceptor where the reaction is essentially in the liquid phase.

TABLE 5

($^{iPr4}$PCP)Ir(C$_2$H$_4$) catalyzed dehydrogenation of η-dodecane [4.4 M] under 4 atm of ethylene [2.4 M] at 240° C.

| Catalyst | Alignment of the vial | Acceptor P [M] | Time Min | Total Olefins mM | Ethane mM % = Total Double bonds[a] | Monoenes 1-Doclecene [mM] Selectivity %[b] | Monoenes Total |
|---|---|---|---|---|---|---|---|
| Complex 7 | Vertical 100 μl | Ethylene 4 atm 2.4 M | 10 | 440 ± 5 | 450 18% | 182 ± 2 42% | 428 ± 6 |
|  |  |  | 40 | 768 ± 11 | 815 33% | 222 ± 2 30% | 726 ± 13 |
|  |  |  | 180 | 1290 ± 2 | 1926 80% | 285 ± 5 30% | 830 ± 3 |

[a]Ethane formed = Total dehydrogenation = Total double bonds formed,
[b]Selectivity = (1-decene/Total monoenes) × 100

Example 5: Dehydrogenation of n-Butane with Propene

As demonstrated in Example 5, it has been found that iridium pincer complex catalyzed dehydrogenation of butane with propene at temperatures below 300° C., for example at 240° C., results in reactions occurring in the gas phase.

Figure 2:
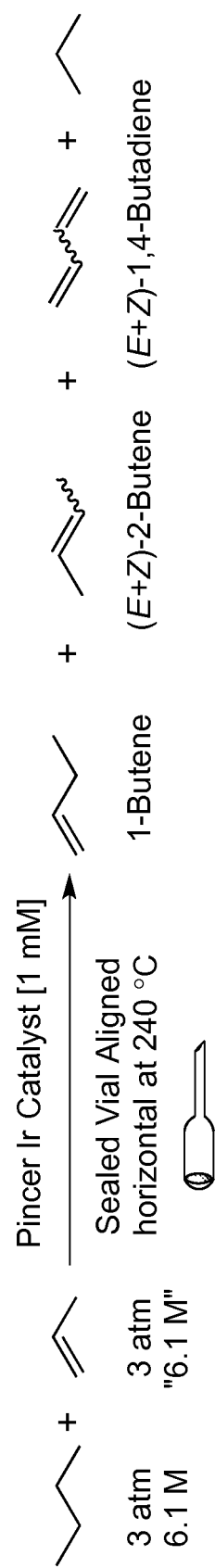
FIG. 2 is a schematic diagram showing the details of the reaction of Example 5.

The transfer dehydrogenation of n-butane with propene in the gas phase was tested with Complex 10: ($^{iPr4}$PCP)Ir. The details of the reaction and the results of the runs are set forth in Table 6 and FIG. 2. High selectivity for 1-butene and significant amounts of butadienes were observed.

TABLE 6

Dehydrogenation of 3 atm of n-butane [6.1 M] catalyzed by pincer iridium complex at propene pressure of 3 atm ("6.1 M") at 240° C.

| Entry | Catalyst 1 mM | Time | Total Olefin TON | Butadiene TON | 1-Butene TON | 1-Butene Fraction (%) |
|---|---|---|---|---|---|---|
| 1 | Complex 10 | 10 | 335 | 40 | 185 | 65 |
|  |  | 40 | 590 | 40 | 370 | 65 |
|  |  | 180 | 680 | 65 | 280 | 45 |

Example 6: Dehydrogenation of n-Pentane with Propene Using Supported Catalyst As demonstrated in Example 6, it has been found that supported iridium pincer complex catalyzed dehydrogenation of pentane with propene at temperatures as low as 200° C. results in reactions occurring in the gas phase with unprecedented rates and TONs. Example 6 also demonstrates supported iridium pincer complexes catalyze dehydrogenation of pentane with propene at temperatures as low as 200° C. with better activity and recyclability than unsupported iridium pincer complex catalysts.

Figure 3:
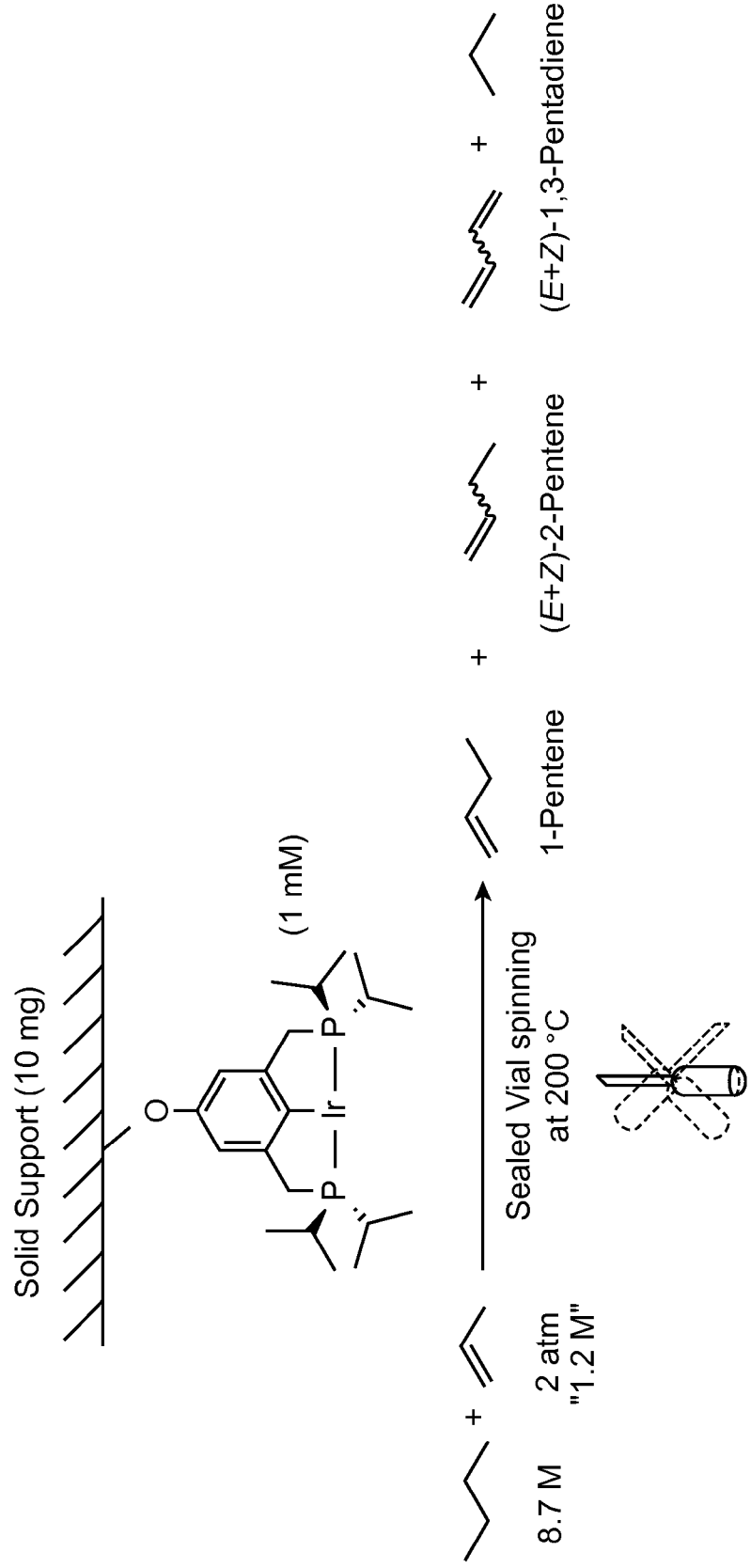
FIG. 3 is a schematic diagram showing the details of the reaction of Example 6.

The transfer dehydrogenation of n-pentane with propene was tested with Complex 11: (p-OK-$^{iPr4}$PCP)Ir(C$_3$H$_6$) immobilized on various solid supports. The details of the reaction and the results of the runs are set forth in Table 7 and FIG. 3.

Table 7 shows the supported iridium pincer complex has the ability to catalyze dehydrogenation of pentane with propene at temperatures as low as 200° C. with unprecedented rates and TONs. While the iridium pincer complex supported on silica gave about 200 TON in 10 minutes, the iridium pincer complex supported on neutral alumina and florisil, respectively, gave almost full conversion in 10 minutes of 1050 and 830 TONs, respectively.

TABLE 7

(p-OK-$^{iPr4}$PCP)Ir catalyzed gas phase dehydrogenation of n-pentane [8.7 M] under 2 atm of propene 37 [1.2 M]" at 200° C. on various solid supports

| Entry | Solid Support | Time (min) | Total Olefins mM =Double bonds[a] | Propane mM % C$_3$ GC[b] | 1-Pentene mM Selectivity%[c] | 2-Pentenes mM E- | Z- | (E + Z)-1,3-Pentadienes mM |
|---|---|---|---|---|---|---|---|---|
| 1 | Silica SiO$_2$ | 10 | 205 ± 5 | 212 17% | 20% | 80 ± 2(40%) | 88 ± 1 | 33 ± 1 | 7 ± 1 |
|  |  | 40 | 448 ± 22 | 478 39% | 37% | 120 ± 5 (29%) | 216 ± 10 | 84 ± 5 | 30 ± 2 |
|  |  | 180 | 496 ± 8 | 536 44% | 40% | 91 ± 1 (20%) | 262 ± 5 | 104 ± 2 | 40 ± 1 |
| 2 | γ-Alumina Al$_2$O$_3$ | 10 | 530 ± 2 | 584 48% | 41% | 138 ± 2 (29%) | 238 ± 2 | 100 ± 1 | 54 ± 2 |
|  |  | 40 | 790 | 878 70% | 65% | 140 (20%) | 410 | 150 | 90 |
|  |  | 180 | 1265 | 1425 115% | 95% | 154 (14%) | 673 | 278 | 160 |
| 3 | Basic Alumina Al$_2$O$_3$ | 10 | 450 ± 5 | 486 40% | 42% | 127 ± 3 (31%) | 205 ± 1 | 80 ± 2 | 34 ± 2 |
|  |  | 40 | 792 ± 25 | 885 70% | 65% | 138 ± 15 (20%) | 410 ± 2 | 152 ± 15 | 92 ± 6 |
|  |  | 180 | 1290 ± 1 | 1460 115% | 95% | 133 ± 10(12%) | 718 ± 20 | 272 ± 10 | 170 ± 5 |
| 4 | Florisil MgO$_3$Si | 10 | 830 ± 2 | 920 75% | 75% | 124 ± 2 (17%) | 440 ± 2 | 174 ± 1 | 90 ± 2 |
|  |  | 40 | 1150 ± 40 | 1273 103% | 95% | 96 ± 4 (10%) | 667 ± 15 | 256 ± 15 | 125 ± 5 |
| 5 | Neutral Alumina Al$_2$O$_3$ | 10 | 1050 | 1190 97% | 90% | 160 (18%) | 550 | 200 | 140 |

[a]Propane formed = Total dehydrogenation = Total double bonds formed, [b]Calculated from ratio of propane to propene as observed by GC, [c]Selectivity = (1-pentene/Total monoenes) x 100s The transfer dehydrogenation of n-pentane with propene with Complex 11: (p-OK-$^{iPr4}$PCP)Ir(C$_3$H$_6$) immobilized on various solid supports was also compared to that of the unsupported complex. The details of the reaction and the results of the runs are set forth in the following Tables 8 and 9. Table 8 shows the supported complexes had higher activity compared to the unsupported complex. Catalyst activity is determined based on rate of reaction, in this case through both TONs and % feedstock consumed. As shown in Table 8, the TONs and conversions are significantly better for the supported complexes compared to the unsupported complex.

Table 9 shows the supported complexes also had better recyclability compared to the unsupported complex. In this example, the volatiles (i.e., C5 hydrocarbons) were evacuated and the catalysts were reused without any regeneration treatment.

TABLE 8

Comparison of activity in the unsupported and supported pincer iridium catalyzed gas phase dehydrogenation of n-pentane [8.7 M] under 2 atm of propene "[1.2 M]" at 200° C.

| Catalyst | Time (min) | Total Olefins mM | Propane mM =Double bonds$^a$ | % C$_3$ GC$^b$ | 1-Pentene mM Selectivity %$^c$ | 2-Pentenes mM E- | Z- | (E + Z)-1,3-Pentadienes mM |
|---|---|---|---|---|---|---|---|---|
| Complex 10 Unsupported (Coating on walls) | 10 | 410 ± 11 | 444 36% | 36% | 153 ± 5 (41%) | 148 ± 2 | 76 ± 1 | 34 ± 2 |
| Complex 11 Unsupported (Coating on walls) | 10 | 225 | 252 20% | 22% | 75 (33%) | 90 | 36 | 26 |
| Complex 11 Supported on γ-Alumina Al$_2$O$_3$ | 10 | 530 ± 2 | 584 48% | 41% | 138 ± 2 (29%) | 238 ± 2 | 100 ± 1 | 54 ± 2 |
| Complex 11 Supported on Florisil MgO$_3$Si | 10 | 830 ± 2 | 920 75% | 75% | 124 ± 2 (17%) | 440 ± 2 | 174 ± 1 | 90 ± 2 |
| Complex 11 Supported on Neutral Alumina Al$_2$O$_3$ | 10 | 1050 | 1190 97% | 90% | 160 (18%) | 550 | 200 | 140 |

TABLE 9

Comparison of recyclability in the unsupported and supported pincer iridium catalyzed dehydrogenation of n-pentane [8.7M] under 2 atm of propene "[1.2M]" at 200° C. after 10 minutes.

| Catalyst | Time (min) | Cycle | Total Olefins mM |
|---|---|---|---|
| Complex 10 Unsupported (Coating on walls) | 10 10 | First Second | 410 ± 11 20 |
| Complex 11 Supported on Basic-Alumina Al$_2$O$_3$ | 10 10 | First Second | 450 ± 5 130 |
| Complex 11 Supported on Neutral Alumina Al$_2$O$_3$ | 10 10 | First Second | 1050 1100 |

Example 7: Dehydrogenation of n-Pentane with Propene Using γ-Alumina Supported Catalyst As demonstrated in Example 7, it has been found that supported iridium pincer complex catalyzed dehydrogenation of pentane with propene is possible at temperatures as low as 160° C.

The transfer dehydrogenation of n-pentane with propene was tested with Complex 11: (p-OK-$^{iPr4}$PCP)Ir(C$_3$H$_6$) immobilized on γ-alumina. The details of the reaction and the results of the runs are set forth in Table 10. The dehydrogenation reaction occurred in the liquid phase at a temperature of only 160° C.

TABLE 10

(p-OK-$^{iPr4}$PCP)Ir catalyzed liquid phase dehydrogenation of n-pentane [8.7 M] under 2 atm of propene "[1.2 M]" at 160° C.

| Catalyst 1 mM | Temp ° C. | t min | Total Olefins | Propane mM =Double bonds[a] | % $C_3$[b] | 1-Pentene mM % Fraction[c] | 2-Pentenes mM E- | 2-Pentenes mM Z- | (E + Z)-1,3- Pentadienes |
|---|---|---|---|---|---|---|---|---|---|
| Complex | 160 | 10 | 36 ± 2 | 36 3% | 3% | 8 ± 1 (22%) | 20 ± 1 | 8 ± 1 | 0 |
| 11 on γ-Alumina | @ 2 atm | 80 | 164 ± 2 | 167 14% | 15% | 14 ± 1 (10%) | 108 ± 1 | 40 ± 1 | 3 ± 1 |
|  |  | 180 | 258 ± 18 | 270 22% | 22% | 30 ± 2 (12%) | 157 ± 10 | 58 ± 4 | 12 ± 1 |
|  |  | 600 | 846 ± 5 | 965 75% | 65% | 105 ± 3 (12%) | 445 ± 10 | 180 ± 4 | 120 ± 2 |

[a]Propane formed = Total dehydrogenation = Total double bonds formed, [b]Calculated from ratio of propane to propene as observed by GC, [c]Selectivity =(1-pentene/Total monoenes) × 100

Vapor Pressure of pentane at 160° C.=18 atm
Total pressure generated by complete vaporization of 100 ul pentane=24 atm

Example 8: Synthesis of $C_6H_4(CH_2(^iPPr)_2)_2$

Dibromo m-xylene (2.00 g, 7.6 mmol) and diisopropylphosphine (1.79 g, 15.1 mmol) were dissolved in 15.0 ml acetone in the glove box. The mixture was refluxed under an Ar atmosphere for 24 hours. The reaction mixture was cooled in an ice bath and the dense white precipitate was separated by cannula filtration. The white solid was vacuum dried and then suspended in a mixture of 35.0 ml benzene and triethylamine (4.2 ml, 30.2 mmol). The reaction mixture was stirred at rt for 60 h. The resulting solution was subjected to cannula filtration. The solvent from the filtrate was removed under reduced pressure to yield 1.8 g (70%) of colorless oil. $^{31}P$ {H} NMR (C6D6, 161.9 MHz): δ 10.19 (s)$^1$H NMR (C6D6, 400 MHz): δ 6.83~6.92 (m, 4H, aromatic), 1.32 (d of sept, $J_{HH}$=5.6 Hz, $J_{PH}$=1.6 Hz, 4H, PCH(CH$_3$)$_2$), 0.73 (d, 5.6 Hz, 12H, PCH(CH$_3$)$_2$), 0.70 (dd, $J_{HH}$=5.6 Hz, $J_{PH}$=1.2 Hz, 12H, PCH(CH$_3$)$_2$)

Example 9: Synthesis of $^{iPr4}$PCPIr(HCl/Br)

Ultra high purity H$_2$ was bubbled into a 20.0 ml toluene solution of [(COD)IrCl]$_2$ (1.78 g, 2.6 mmol) and C$_6$H$_4$(CH$_2$($^i$PPr)$_2$)$_2$ (1.80 g, 5.3 mmol) for about 15 minutes. The reaction mixture was then stirred at 80° C. under an H$_2$ atmosphere for 15 h. Solvent was removed from the resulting red solution to yield a red solid. The red solid was then stirred with 100.0 ml pentane for 30 minutes. The solution was cannula filtered and filtrate was collected. The extraction was repeated five more times and filtrate was collected. Then the residue was further stirred with 100 ml pentane overnight and extracted. All filtrate were mixed and the solvent was evaporated to obtain a red solid in 51% yield (1.55 g). NMR analysis indicated the red solid to be 5:1 mixture of $^{iPr4}$PCPIr(HCl) and $^{iPr4}$PCPIr(HBr).

31P NMR (C6D6, 161.9 MHz): δ 58.40 (HBr complex, d, 12.3 Hz), δ 58.44 (HCl complex, d, 12.3 Hz)

1H NMR (C6D6, 400 MHz): δ 6.95 (s, 3H, PCP), 2.84 (d of vt, JPH=4.0 Hz, JHH=17.6 Hz, 2H, CH2P), 2.73 (d of vt, JPH=4.4 Hz, JHH=17.6 Hz, 2H, CH2P), 2.71 (m, 2H, PCH(CH3)2), 1.96 (m, 2H, PCH(CH3)2) 1.19 (app. Sext (dqt), 7.7 Hz, 12H, PCH(CH3)2), 0.86~0.93 (m, 12H, PCH (CH3)2), [−36.25 (HCl complex) and −38.25 (HBr complex)] (t, JPH=13.2 Hz, 1H, IrH)

Example 10: Synthesis of Complex 7

Ethylene was bubbled for about 15 minutes into a reddish 60.0 ml pentane solution of $^{iPr4}$PCPIr(HCl/Br) (0.21 g, 0.4 mmol) whereupon the solution turns colorless. To the above solution 1M LiBEt3H (0.37 ml, 0.4 mmol) was added drop wise under ethylene atmosphere. The colorless solution then gradually turns brownish. The reaction mixture was stirred overnight under ethylene atmosphere. Removal of pentane from the filtrate obtained from cannula filtration yields 0.20 g of a brown solid in quantitative yield. NMR and elemental analysis indicate the formation of expected compound in >99% purity. Crystals suitable for X-ray analysis were grown by slow evaporation of a 10 mg solution of Complex 7: ($^{iPr4}$PCP)Ir(C$_2$H$_4$) in 1.0 ml pentane.

31P NMR (C6D6, 161.9 MHz): 51.45

1H NMR (C6D6, 400 MHz): 7.45 7.32 (m, 3H, Arene H), 3.18 (t, J=3.8 Hz, 4H, CH2P), 3.11 (t, J=3.0 Hz, 4H, Ir(C2H4)), 2.15 (m, 4H, PCH(CH3)2), 1.15 (dd, J=14.7, 7.2 Hz, 12H, PCH(CH3)2), 1.00 (dd, J=13.2, 6.7 Hz, 12H, PCH(CH3)2).

Calcd for C22H39IrP2: C, 47.38; H, 7.05. Found: C, 48.23; H, 7.23

Example 11: Synthesis of Complex 12

Introducing H$_2$ to a pentane solution of Complex 7: ($^{iPr4}$PCP)Ir(C$_2$H$_4$) into atmosphere results in formation of Complex 12: ($^{iPr4}$PCP)IrH$_4$ in quantitative yields as an orange solid.

31P NMR (p-xylene-d10, 161.9 MHz): δ 54.70

1H NMR (p-xylene-d10, 400 MHz): δ 7.02 (s, 3H, PCP), 3.17 (vt, JPH=4.0 Hz, 4H, CH2P), 1.55 (m, 4H, PCH(CH3) 2), 1.03 (app. qt, 7.5 Hz, 12H, PCH(CH3)2) 0.97 (app. qt, 7.1 Hz, 12H, PCH(CH3)2), −9.40 (t, 10.2 Hz, IrH4)

Example 12: Synthesis of Complex 11

Figure 4:
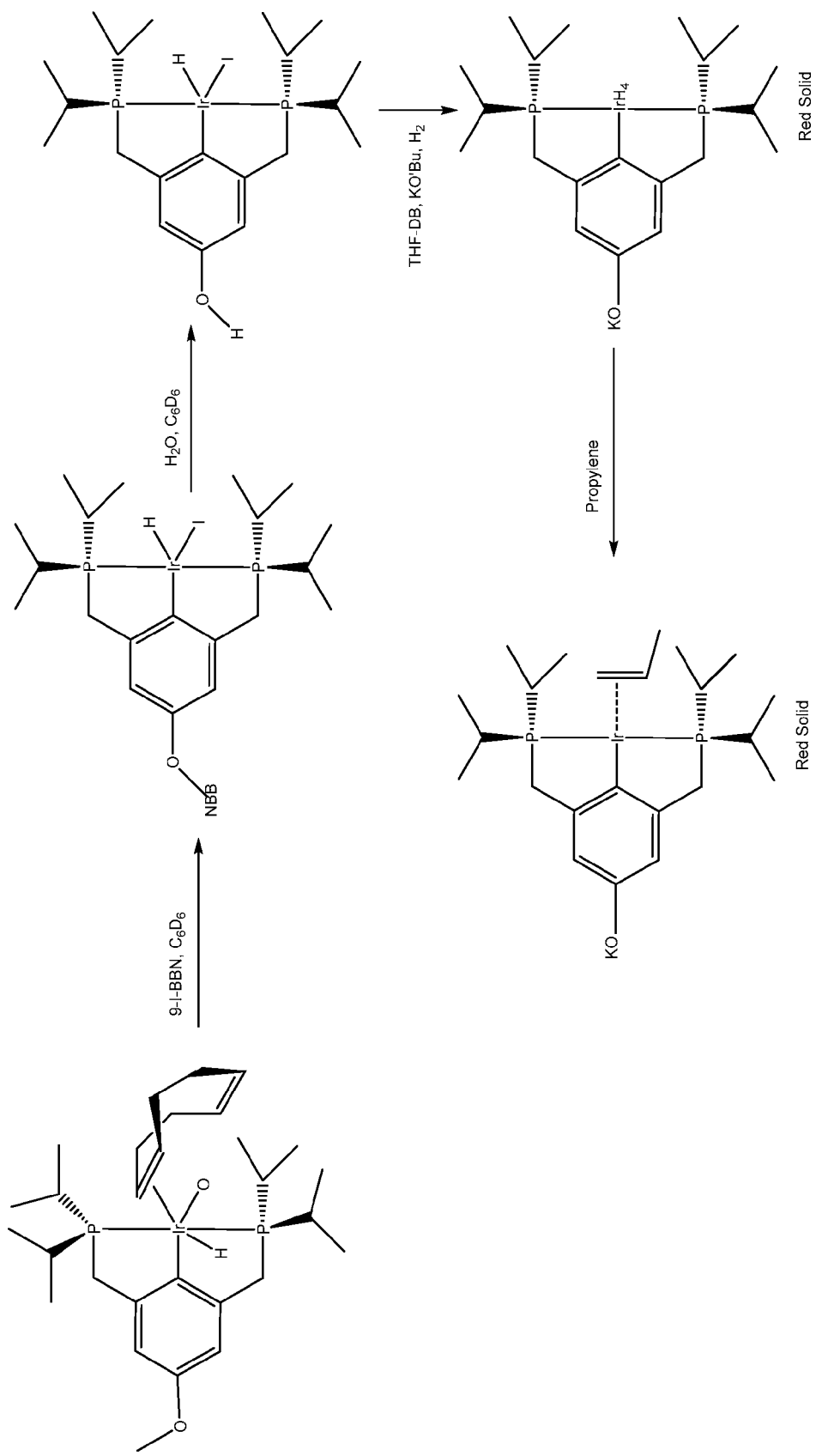
FIG. 4 illustrates the synthesis procedure of Example 12.

Complex 11: (p-OK-$^{iPr4}$PCP)Ir(C$_3$H$_6$) was synthesized as illustrated in FIG. 4. Synthesized from (p-OMe$^{iPr4}$PCP)Ir) HCl following a literature procedure reported for the synthesis of (p-OK-$^{tBu4}$POCOP)Ir(C$_2$H$_4$) (See Huang, Z.; Brookhart, M.; Goldman, A. S.; Kundu S.; Ray, A.; Scott, S. L.; Vicente, B. C.; Adv. Synth. Catal. 2009, 351, 188).

Example 13: Immobilization of Complex 11 onto Solid Supports

A 1 mM stock solution of (p-OK-$^{iPr4}$PCP)Ir(C$_3$H$_6$) was prepared in THF. About 100 µl of this red colored stock solution was transferred to sealable 1.5 ml vials containing 10 mg of solid support. After stirring for about five minutes the red color of the solution decolorizes and the solid support turns red in color. THF was evacuated from the vials to obtain a free flow red solid. The vials were refilled with 100 µl pentane. The solution is colorless. The vials were then charged with propene, flame sealed and subjected to interval free heating by spinning in a rotisserie oven at 200° C.

Example 14: Acceptorless Dehydrogenation of n-Dodecane

Figure 5:
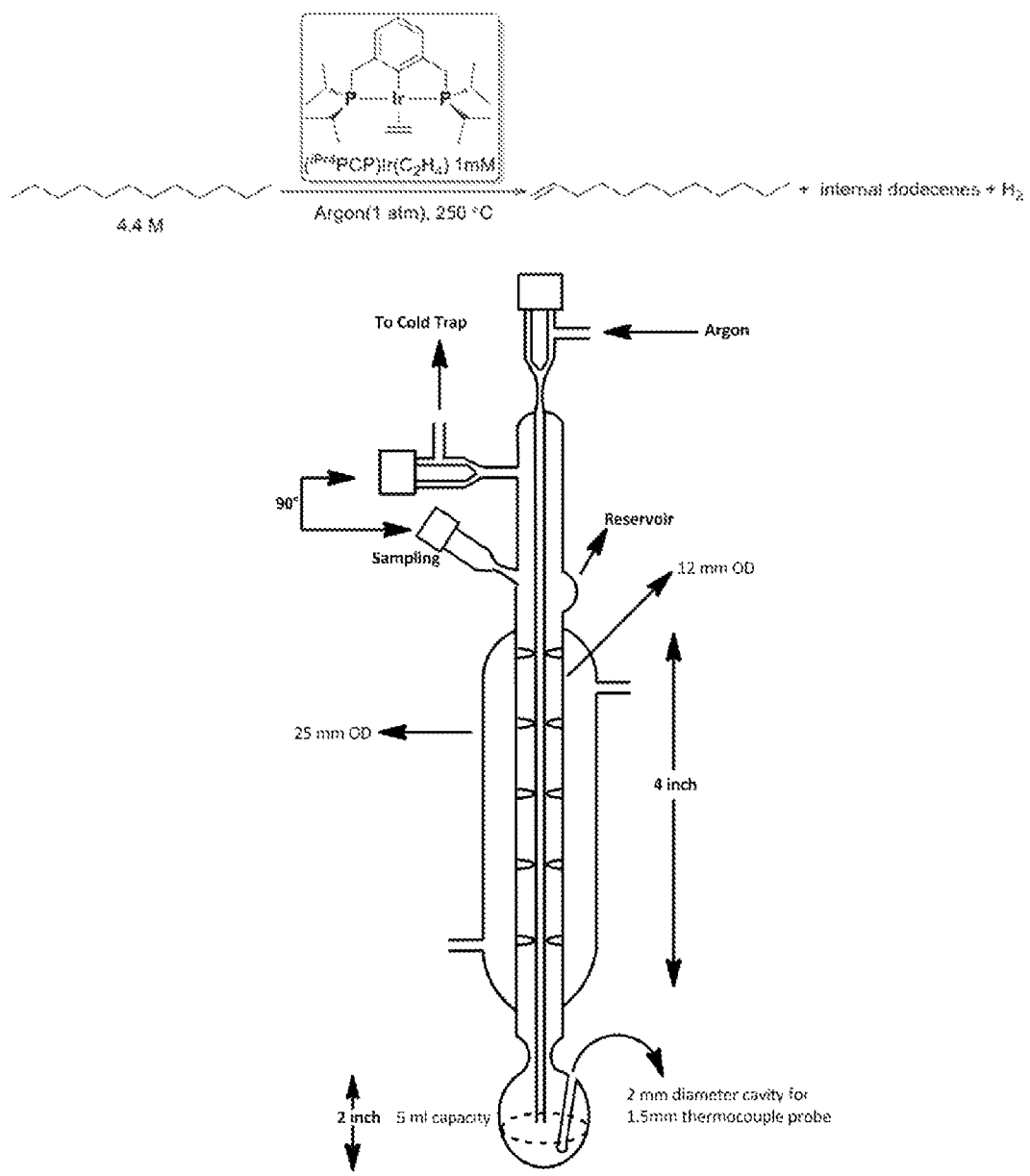
FIG. 5 illustrates acceptorless dehydrogenation of n-dodecane as described in Example 14.

Acceptorless dehydrogenation of n-dodecane was accomplished as illustrated in FIG. 5. The complex ($^{iPr4}$PCP)Ir (C$_2$H$_4$) (1.2 mg, 2 μmoles) was dissolved in anhydrous degassed n-dodecane (2.0 ml, 9 mmol) in the acceptorless vessel inside a glove box under argon atmosphere. The vessel was then sealed and brought out of the glove box. The vessel was connected to a Schlenk line and introduced to Argon atmosphere. The zero time reading was obtained by GC analysis of the reaction mixture. The reaction mixture was then heated at 250° C. by continuously bubbling argon through the system to sparge out the hydrogen that is released during the reaction. The outlet of the gas flow was connected to cold finger at −15° C. to trap any volatiles. At regular intervals, an aliquot was withdrawn from the reactor, and the contents were analyzed by GC. Periodically the contents of the cold finger were also analyzed.

TABLE 11

Acceptorless Dehydrogenation of Pentadecane and Dodecane

| Reaction condition | Time (h) | Total Olefins (mM) |
|---|---|---|
| $^{4iPr}$PCP)Ir(C$_2$H$_4$)(2.0 mM) + 1 ml dodecane at 250° C. oil bath bp = 217° C. | 3<br>6 | 28<br>33 |
| (OMe—$^{4iPr}$PCP)Ir(C$_2$H$_4$)(1.0 mM) + 2 ml dodecane at 220° C. oil bath bp = 217° C. | 3<br>6<br>9 | 15<br>19<br>22 |
| (OMe—$^{4iPr}$PCP)Ir(C$_2$H$_4$)(1.0 mM) + 2 ml pentadecane at 250° C. oil bath (bp = 270° C.) | 1<br>3 | 20<br>27 |
| (OMe—$^{4iPr}$PCP)Ir(C$_2$H$_4$)(1.0 mM) + 2 ml dodecane at 250° C. oil bath bp = 217° C. | 1<br>3<br>6 | 17<br>33<br>43 |
| (OMe—$^{4iPr}$PCP)Ir(C$_2$H$_4$)(1.0 mM) + 2 ml dodecane at 260° C. oil bath bp = 217° C. | 1<br>3<br>6 | 62<br>75<br>98 |
| (OMe—$^{4iPr}$PCP)Ir(C$_2$H$_4$)(1.0 mM) + 2 ml dodecane + 100 mg SiC boiling chips at 250° C. oil bath bp = 217° C. | 1<br>3<br>6 | 32<br>52<br>66 |

Various modifications and alterations of the process disclosed herein will become apparent to those skilled in the art without departing from the scope and spirit of the process disclosed herein. Other objects and advantages will become apparent to those skilled in the art from a review of the preceding description.

A number of patent documents and non-patent documents are cited in the foregoing specification in order to describe the state of the art to which the process disclosed herein pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed process. All iridium pincer complex catalysts and methods of use thereof embodied herein can, in alternate embodiments, be more specifically defined by any of the transitional terms "comprising", "consisting essentially of" and "consisting of".

That which is claimed is:
1. A process for preparing an alpha-olefin by dehydrogenation of at least one alkane, comprising the steps of:
   providing an alkane feedstock in the gaseous phase comprising at least one alkane;
   contacting the alkane feedstock in the gaseous phase with an iridium pincer complex in the presence of a gaseous hydrogen acceptor selected from the group consisting of ethylene, propene, or mixtures thereof, wherein the iridium pincer complex is selected from the group consisting of

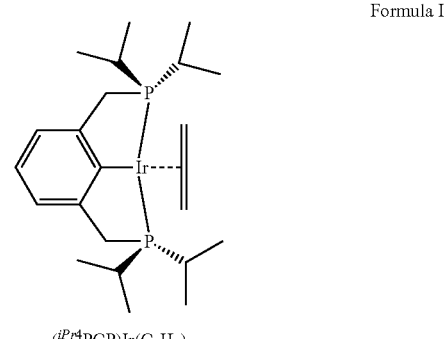

($^{iPr4}$PCP)Ir(C$_2$H$_4$), Formula I

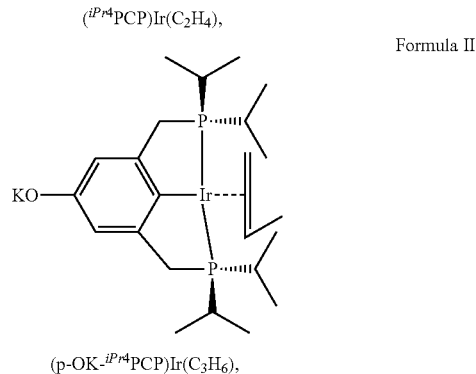

(p-OK-$^{iPr4}$PCP)Ir(C$_3$H$_6$), Formula II and mixtures thereof; and
   recovering an alpha-olefin product.
2. The process of claim 1, wherein the at least one alkane in the gaseous phase is selected from the group consisting of butane, pentane, octane, nonane, decane, dodecane, and mixtures thereof.
3. The process of claim 1, wherein the iridium pincer complex is unsupported.
4. The process of claim 1, wherein the iridium pincer complex is immobilized on a solid support.
5. The process of claim 4, wherein the solid support is selected from the group consisting of silica, γ-alumina, basic alumina, florisil, and neutral alumina.
6. The process of claim 5, wherein the solid support is florisil or neutral alumina.

7. The process of claim 1, wherein the contacting is performed at a reaction temperature of less than 300° C.

8. The process of claim 7, wherein the reaction temperature is in a range of 160° C.-260° C.

9. The process of claim 7, wherein the reaction temperature is about 240° C.

10. The process of claim 7, wherein the reaction temperature is about 200° C.

11. The process of claim 7, wherein the reaction temperature is about 160° C.

12. The process claim 1, wherein the contacting is performed for up to 24 hours.

13. The process of claim 1, wherein the contacting is performed for 10-100 minutes.

* * * * *